United States Patent
Baker et al.

(10) Patent No.: US 12,246,057 B2
(45) Date of Patent: Mar. 11, 2025

(54) TRANSMEMBRANE STEM CELL FACTOR (tm-SCF) LIPID NANOCARRIERS AND METHODS OF USE THEREOF

(71) Applicant: BOARD OF REGENTS, THE UNIVERSITY OF TEXAS SYSTEM, Austin, TX (US)

(72) Inventors: Aaron Baker, Austin, TX (US); Eri Takematsu, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1185 days.

(21) Appl. No.: 17/047,135

(22) PCT Filed: Apr. 12, 2019

(86) PCT No.: PCT/US2019/027192
§ 371 (c)(1),
(2) Date: Oct. 13, 2020

(87) PCT Pub. No.: WO2019/200240
PCT Pub. Date: Oct. 17, 2019

(65) Prior Publication Data
US 2021/0145931 A1 May 20, 2021

Related U.S. Application Data

(60) Provisional application No. 62/657,153, filed on Apr. 13, 2018.

(51) Int. Cl.
A61P 43/00 (2006.01)
A61K 38/17 (2006.01)
A61K 47/69 (2017.01)

(52) U.S. Cl.
CPC ........ *A61K 38/177* (2013.01); *A61K 47/6925* (2017.08); *A61P 43/00* (2018.01)

(58) Field of Classification Search
None
See application file for complete search history.

(56) References Cited

U.S. PATENT DOCUMENTS

| | | |
|---|---|---|
| 5,767,074 A | 6/1998 | Besmer et al. |
| 6,248,353 B1 | 6/2001 | Singh |
| 6,635,802 B1 | 10/2003 | Piedrahita et al. |
| 7,048,949 B2 | 5/2006 | Sligar et al. |
| 7,083,958 B2 | 8/2006 | Sligar et al. |
| 7,575,763 B2 | 8/2009 | Sligar et al. |
| 7,592,008 B2 | 9/2009 | Sligar et al. |
| 7,622,437 B2 | 11/2009 | Morrissey et al. |
| 7,662,410 B2 | 2/2010 | Sligar et al. |
| 7,691,414 B2 | 4/2010 | Sligar et al. |
| 8,404,653 B2 | 3/2013 | Zsebo |
| 8,524,655 B2 | 9/2013 | Zhao et al. |
| 2004/0053384 A1 | 3/2004 | Sligar et al. |
| 2006/0058339 A1 | 3/2006 | Ibrahim et al. |
| 2009/0220588 A1 | 9/2009 | Edelman et al. |
| 2015/0284397 A1 | 10/2015 | Lin et al. |
| 2017/0189479 A1 | 7/2017 | Baker et al. |

FOREIGN PATENT DOCUMENTS

| | | |
|---|---|---|
| CA | 2409448 A1 | 11/2001 |
| CN | 1241210 A | 1/2000 |
| WO | 2004052177 A2 | 6/2004 |

OTHER PUBLICATIONS

Bayburt, Timothy H., and Stephen G. Sligar. "Membrane protein assembly into Nanodiscs." FEBS letters 584.9 (2010): 1721-1727.
Carter, Paul J. "Introduction to current and future protein therapeutics: a protein engineering perspective." Experimental cell research 317.9 (2011): 1261-1269.
Cui, Lili, et al. "Repairing the brain by SCF+ G-CSF treatment at 6 months postexperimental stroke: mechanistic determination of the causal link between neurovascular regeneration and motor functional recovery." ASN neuro 8.4 (2016): 1759091416655010.
Das, et al. Overcoming disease-induced growth factor resistance in therapeutic angiogenesis using recombinant coreceptors delivered by a liposomal system. Biomaterials 35 (2014) 196e205.
Friel, Jutta, et al. "Role of the Stem Cell Factor (SCF) Receptor and the Alternative Forms of its Ligand (SCF) in the Induction of Long Term Growth by Stroma Cells." Leukemia (08876924) 11 (1997).
Hogaboam, Cory, et al. "Novel role of transmembrane SCF for mast cell activation and eotaxin production in mast cell-fibroblast interactions." The Journal of Immunology 160.12 (1998): 6166-6171.
Ishikawa, Kiyotake, et al. "Stem cell factor gene transfer improves cardiac function after myocardial infarction in swine." Circulation: Heart Failure 8.1 (2015): 167-174.
Matsui, Junji, et al. "Stem cell factor/c-kit signaling promotes the survival, migration, and capillary tube formation of human umbilical vein endothelial cells." Journal of Biological Chemistry 279.18 (2004): 18600-18607.
Zhao, Li-Ru, et al. "Beneficial effects of hematopoietic growth factor therapy in chronic ischemic stroke in rats." Stroke 38.10 (2007): 2804-2811.
Translation of CN1241210A.
International Preliminary Report on Patentability issued for Application No. PCT/US2019/027192, dated Oct. 22, 2020.

(Continued)

*Primary Examiner* — Alton N Pryor
(74) *Attorney, Agent, or Firm* — Meunier Carlin & Curfman LLC

(57) ABSTRACT

The present invention relates to compositions comprising transmembrane stem cell factor (tmSCF) polypeptide embedded in a lipid vesicle and methods of use thereof. In some embodiments, the lipid vesicle is a nanocarrier. Disclosed herein is a method for promoting angiogenesis in a subject, comprising administering to a subject in need thereof an effective amount of a composition comprising a tmSCF polypeptide embedded in a lipid vesicle. Disclosed herein is a method for treating a subject with peripheral vascular disease (PVD), comprising administering to a subject in need thereof a therapeutically effective amount of a composition comprising a tmSCF polypeptide.

12 Claims, 10 Drawing Sheets
Specification includes a Sequence Listing.

(56) References Cited

OTHER PUBLICATIONS

International Search Report and Written Opinion dated Jul. 3, 2019, from International Application No. PCT/US2019/027192, 11 pages.
Chai, M. et al. "Insights into the transmembrane helix associations of kit ligand by molecular dynamics simulation and TOXCAT", Proteins 2017; 85:1362-1370.
Broudy, V. "Stem Cell Factor and Hematopoiesis", Blood, vol. 90, No. 4, Aug. 15, 1997.

TRANSMEMBRANE STEM CELL FACTOR (tm-SCF) LIPID NANOCARRIERS AND METHODS OF USE THEREOF

CROSS REFERENCE TO RELATED APPLICATIONS

This application is a National Phase Application of PCT/US2019/027192, filed Apr. 12, 2019, which claims the benefit of U.S. Provisional Patent Application Ser. No. 62/657,153 filed Apr. 13, 2018, the disclosures of which are expressly incorporated herein by reference.

FIELD

The present invention relates to compositions comprising transmembrane stem cell factor (tmSCF) lipid nanocarriers and methods of use thereof.

BACKGROUND

Peripheral vascular disease (PVD) is very common and present in about 16% of the general population over 65 years of age. Its most severe form is known as critical limb ischemia, which requires patients to undergo an amputation of their limb. Current standard of care includes endovascular interventions such as angioplasty/stenting or surgical bypass of stenosed arteries. Bypass surgeries are limited by the need to harvest veins/arteries from other areas in the patient or to use synthetic grafts that perform poorly when used with small diameters. Moreover, in cases of diffuse vascular disease, bypass surgery is less effective. Endovascular stent placement also has unsatisfactory outcomes in peripheral vessels, in contrast to stenting in the coronary vasculature of the heart, and suffer from high rates of restenosis (closure) over time.

A recently emerging strategy for treating ischemia in PVD is to use therapies to facilitate angiogenesis, the growth of new blood vessels. Stem cell factor (SCF) is a protein that interacts with the receptor c-Kit found on stem cells and many other cell types including endothelial cells. It can have direct effects on endothelial cells to induce angiogenesis but can also act to stimulate the bone marrow to make circulating cells called endothelial progenitor cells that home to the site of injury and can incorporate into vasculature. Transmembrane stem cell factor is a form of SCF that can have different activity/signaling compared to soluble SCF. Soluble SCF has been explored in animal clinical trials for stroke; however, the clinical application has been limited due to a hyperreactivity (mast cell degranulation) response that occurs in some patients. What is needed are improved compositions and methods for delivery of SCF to subjects to improve angiogenesis and to treat peripheral vascular disease (PVD).

The compositions and methods disclosed herein address these and other needs.

SUMMARY

Disclosed herein are novel compositions comprising transmembrane stem cell factor (tmSCF), a membrane linked form of SCF, delivered as a proteoliposome or lipid nanodisc carrier. In the past, tmSCF has not been used as a therapeutic protein. This may be in part because it is difficult to produce tmSCF as a recombinant protein and tmSCF has poor solubility.

Disclosed herein, the inventors have shown that tmSCF delivered in a lipid carrier can improve activity in models of endothelial proliferation and tube formation. In addition, tmSCF delivered in a lipid carrier can improve revascularization in ischemic tissues following femoral artery ligation in mice. Surprisingly, in contrast to soluble SCF, no hyperreactivity was observed in the mice treated with tmSCF proteoliposomes or nanodiscs.

In some aspects, disclosed herein is a composition comprising a transmembrane stem cell factor (tmSCF) polypeptide embedded in a lipid vesicle.

In some embodiments, the lipid vesicle comprises a lipid bilayer. In some embodiments, the lipid vesicle comprises a phospholipid.

In some embodiments, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, phosphatidyl choline (PC); phosphatidyl ethanolamine (PE), phosphatidyl inositol (PI); dihexanoyl phosphatidyl choline (DHPC), dipalmitoyl phosphatidyl ethanolamine, dipalmitoyl phosphatidyl inositol; dimyristoyl phosphatidyl ethanolamine; dimyristoyl phosphatidyl inositol; dihexanoyl phosphatidyl ethanolamine; dihexanoyl phosphatidyl inositol; 1-palmitoyl-2-oleoyl-phosphatidyl ethanolamine; 1-palmitoyl-2-oleoyl-phosphatidyl inositol, and mixtures thereof.

In some embodiments, the phospholipid is selected from the group consisting of 1,2-dioleoyl-sn-glycero-3-phosphocholine (DOPC), 1,2-dioleoyl-sn-glycero-3-phosphoethanolamine (DOPE), sphingomyelin, and mixtures thereof.

In some embodiments, the lipid vesicle comprises a sterol. In some embodiments, the sterol is selected from the group consisting of cholesterol, fecosterol, sitosterol, ergosterol, campesterol, stigmasterol, brassicasterol, and mixtures thereof.

In some embodiments, the lipid vesicle comprises 1,2-dioleoyl-sn-glycero-3-phosphocholine (DOPC), 1,2-dioleoyl-sn-glycero-3-phosphoethanolamine (DOPE), sphingomyelin, and cholesterol. In some embodiments, the lipid vesicle comprises 1,2-dioleoyl-sn-glycero-3-phosphocholine (DOPC), 1,2-dioleoyl-sn-glycero-3-phosphoethanolamine (DOPE), sphingomyelin, and cholesterol, in a ratio of about 2:1:1:1, respectively.

In some embodiments, the lipid vesicle is from about 20 nm to about 400 nm in size.

In some embodiments, the transmembrane stem cell factor (tmSCF) polypeptide is human tmSCF, or a variant thereof. In some embodiments, the transmembrane stem cell factor (tmSCF) polypeptide comprises SEQ ID NO:1, or an amino acid sequence that is at least 65% identical to SEQ ID NO:1.

In some embodiments, the composition is encapsulated in a biodegradable microcapsule or microbead. In some embodiments, the microcapsule or microbead comprises a biocompatible hydrogel. In some embodiments, the biocompatible hydrogel comprises a polysaccharide. In some embodiments, the biocompatible hydrogel comprises alginate. In some embodiments, the microcapsule or microbead is from 1 µm in diameter up to 3 mm in diameter.

In some aspects, disclosed herein is a method for promoting angiogenesis in a subject, comprising administering to a subject in need thereof an effective amount of a composition comprising a transmembrane stem cell factor (tmSCF) polypeptide embedded in a lipid vesicle.

In some embodiments, the subject has been diagnosed with peripheral vascular disease (PVD), a chronic wound, an ischemic cardiovascular disorder, or a cerebrovascular disorder.

In some aspects, disclosed herein is a method for treating a subject with peripheral vascular disease (PVD), comprising administering to a subject in need thereof a therapeutically effective amount of a composition comprising a transmembrane stem cell factor (tmSCF) polypeptide embedded in a lipid vesicle.

In some aspects, disclosed herein is a lipid nanodisc composition comprising: a membrane scaffold protein; a lipid; and a transmembrane stem cell factor (tmSCF) polypeptide.

In some embodiments, the lipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, phosphatidyl choline (PC); phosphatidyl ethanolamine (PE), phosphatidyl inositol (PI); dihexanoyl phosphatidyl choline (DHPC), dipalmitoyl phosphatidyl ethanolamine, dipalmitoyl phosphatidyl inositol; dimyristoyl phosphatidyl ethanolamine; dimyristoyl phosphatidyl inositol; dihexanoyl phosphatidyl ethanolamine; dihexanoyl phosphatidyl inositol; 1-palmitoyl-2-oleoyl-phosphatidyl ethanolamine; 1-palmitoyl-2-oleoyl-phosphatidyl inositol, and mixtures thereof.

In some embodiments, the membrane scaffold protein to lipid weight ratio is about 1:65. In some embodiments, the membrane scaffold protein comprises a 1D1 protein.

In some embodiments, the lipid vesicle is from about 10 nm to about 400 nm in size.

In some embodiments, the transmembrane stem cell factor (tmSCF) polypeptide is human tmSCF, or a variant thereof. In some embodiments, the transmembrane stem cell factor (tmSCF) polypeptide comprises SEQ ID NO:1, or an amino acid sequence that is at least 65% identical to SEQ ID NO:1.

In some embodiments, the composition is encapsulated in a biodegradable microcapsule or microbead. In some embodiments, the microcapsule or microbead comprises a biocompatible hydrogel. In some embodiments, the biocompatible hydrogel comprises a polysaccharide. In some embodiments, the biocompatible hydrogel comprises alginate. In some embodiments, the microcapsule or microbead is from 1 µm in diameter up to 3 mm in diameter.

In some aspects, disclosed herein is a method for promoting angiogenesis in a subject, comprising administering to a subject in need thereof an effective amount of a composition comprising: a membrane scaffold protein; a lipid; and a transmembrane stem cell factor (tmSCF) polypeptide.

In some embodiments, the subject has been diagnosed with peripheral vascular disease (PVD), a chronic wound, an ischemic cardiovascular disorder, or a cerebrovascular disorder.

In some aspects, disclosed herein is a method for treating a subject with peripheral vascular disease (PVD), comprising administering to a subject in need thereof a therapeutically effective amount of a composition comprising: a membrane scaffold protein; a lipid; and a transmembrane stem cell factor (tmSCF) polypeptide.

BRIEF DESCRIPTION OF THE DRAWINGS

The accompanying figures, which are incorporated in and constitute a part of this specification, illustrate several aspects described below.

DETAILED DESCRIPTION

Figure 1:
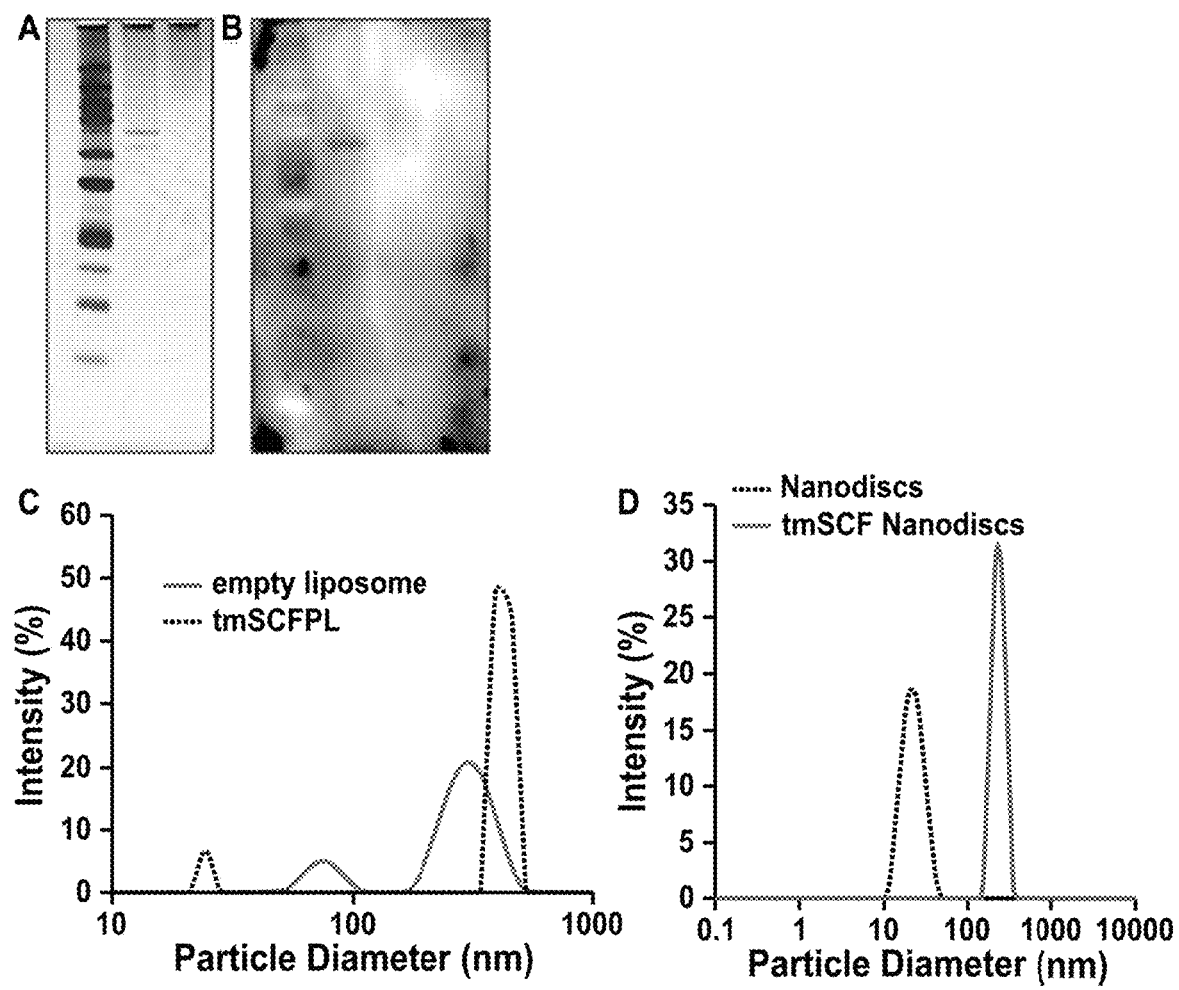
FIG. 1. Characterization of tmSCF liposomes and nanodiscs. (A) Silver staining image of purified tmSCF protein. (B) Western blot image of purified tmSCF Protein. (C) DLS results of empty liposome and tmSCFPL. Main peaks for empty liposome and tmSCFPL are around 300 nm and 400 nm, respectively. (D) DLS results of empty liposome and tmSCFPL. Main peak for empty nanodisc and tmSCFND are around 20-30 nm and 150 nm, respectively FIG. 2. TEM and cryo-EM images of empty liposome, tmSCFPL, empty nanodisc, and tmSCFND. Lipid bilayers are seen in cryo-EM images. Size scale is 100 nm.

Disclosed herein are novel compositions comprising transmembrane stem cell factor (tmSCF), a membrane linked form of SCF, delivered as a proteoliposome or lipid nanodisc carrier. In the past, tmSCF has not been used as a therapeutic protein. This may be in part because it is difficult to produce tmSCF as a recombinant protein and has poor solubility.

Disclosed herein, the inventors have shown that tmSCF delivered in a lipid carrier can improve activity in models of endothelial proliferation and tube formation. This allows tmSCF be delivered in much higher concentrations due to the prevention of aggregation. In addition, tmSCF delivered in a lipid carrier can improve revascularization in ischemic tissues following femoral artery ligation in mice.

Current standard of care for peripheral artery disease (PAD)/peripheral vascular disease (PVD) includes endovascular stent placement and surgical bypass of stenosed arteries, which are invasive methods. Therapeutic angiogenesis with an injectable treatment allows the growth of microvasculature to create a more durable solution that is less invasive and can be used repeatedly on patients that currently cannot be treated with bypass or endovascular interventions.

In comparison to stenting or bypass surgery, the injectable therapy using tmSCF in a lipid carrier allows the regrowth of collateral vessels that can restore blood perfusion and protect the patient from formation of non-healing ulcers or the further development of tissue ischemia. This creates a more durable solution to peripheral vascular disease in comparison to stenting or bypass surgery, both of which fail due to restenosis (reclosure) of the vessels over time.

In comparison to other growth factor therapies, such as FGF-2, VEGF or PDGF-BB, tmSCF has the advantage of acting on the bone marrow, tissue resident stem cells and native vasculature. Thus, these multiple activities make tmSCF more active in therapy resistant patients with poor vascular growth.

Finally, previous concerns with soluble SCF therapies was their ability to activate mast cells. Surprisingly, and in contrast to soluble SCF, no hyperreactivity was observed in the mice with treatment with the tmSCF proteoliposomes or tmSCF nanodiscs described herein.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

As used herein, the term "about" is understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The term "polypeptide" or "protein" refers to a compound made up of a single chain of D- or L-amino acids or a mixture of D- and L-amino acids joined by peptide bonds.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "subject" or "host" can refer to living organisms such as mammals, including, but not limited to humans, livestock, dogs, cats, and other mammals Administration of the therapeutic agents can be carried out at dosages and for periods of time effective for treatment of a subject. In some embodiments, the subject is a human The term "alginate" refers to linear polysaccharides formed from β-D-mannuronate and β-L-guluronate in any M/G ratio, as well as salts and derivatives thereof.

The term "biocompatible" refers to a material and any metabolites or degradation products thereof that are generally non-toxic to the recipient and do not cause any significant adverse effects to the subject.

The term "hydrogel" refers to a substance formed when an organic polymer (natural or synthetic) is cross-linked via covalent, ionic, or hydrogen bonds to create a three-dimensional open-lattice structure which entraps water molecules to form a gel. Biocompatible hydrogel refers to a polymer that forms a gel which is not toxic to living cells, and allows sufficient diffusion of oxygen and nutrients to the entrapped cells to maintain viability.

The term "lipid vesicle" refers to a small vesicle composed of various types of lipids, phospholipids and/or surfactant.

The term "liposome" refers to vesicle composed of a lipid bilayer.

The term "micelle" refers to vesicle composed of a lipid monolayer.

The term "microcapsule" refers to a particle or capsule having a mean diameter of about 50 μm to about 1000 μm, formed of a cross-linked hydrogel shell surrounding a biocompatible matrix. The microcapsule may have any shape suitable for cell encapsulation. The microcapsule may contain one or more cells dispersed in the biocompatible matrix, cross-linked hydrogel, or combination thereof, thereby "encapsulating" the cells.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

The term "proteovesicle" or "proteoliposome" refers to a lipid vesicle or particle comprising a protein embedded in the membrane or attached to its surface.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having at least 65%, 70%, 75%, 80%, 85%, 86%, 87 88%, 89%, 90%, 91%, 92%, 93%, 94%, 95%, 96%, 97%, 98%, or 99% sequence identity to a reference sequence.

Transmembrane Stem Cell Factor (tmSCF) Proteoliposomes

Proteoliposomes (PLs) are made of a lipid bilayer and have spherical shape. PLs (comprising tmSCF) are generally about 200-400 nm in size. In some embodiments, four types of lipids (DOPC, DOPE, cholesterol and sphingomyelin) are used to compose PLs to closely mimic the cell membrane. The functional protein, tmSCF, is inserted in the lipid bilayer. Surrounded by the lipid bilayer, they are not only protected from enzymatic activity and aggregation, but also have greater activity since their environment is close to their native one (cell membrane is also composed of a lipid bilayer).

In some aspects, disclosed herein is a composition comprising a transmembrane stem cell factor (tmSCF) polypeptide embedded in a lipid vesicle.

In some embodiments, the lipid vesicle comprises a lipid bilayer. In some embodiments, the lipid vesicle comprises a phospholipid. In some embodiments, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, phosphatidyl choline (PC); phosphatidyl ethanolamine (PE), phosphatidyl inositol (PI); dihexanoyl phosphatidyl choline (DHPC), dipalmitoyl phosphatidyl ethanolamine, dipalmitoyl phosphatidyl inositol; dimyristoyl phosphatidyl ethanolamine; dimyristoyl phosphatidyl inositol; dihexanoyl phosphatidyl ethanolamine; dihexanoyl phosphatidyl inositol; 1-palmitoyl-2-oleoyl-phosphatidyl ethanolamine; 1-palmitoyl-2-oleoyl-phosphatidyl inositol, and mixtures thereof.

In some embodiments, the lipid vesicle may comprise phospholipids, glycolipids, steroids, or synthetic lipid analogues (e.g., amphipathic, synthethic polymers, such as poly(2-methyl-2-oxazoline) (PMOZ) and poly(2-ethyl-2-oxazoline) (PEOZ)). The lipid vesicle may be a liposome, which is a general category of vesicle that may comprise one or more lipid bilayers surrounding an aqueous space. Methods for liposome production are well known in the art (see U.S. Pat. No. 6,248,353, for example).

In some embodiments, the phospholipid is selected from the group consisting of 1,2-dioleoyl-sn-glycero-3-phosphocholine (DOPC), 1,2-dioleoyl-sn-glycero-3-phosphoethanolamine (DOPE), sphingomyelin, and mixtures thereof.

In some embodiments, the lipid vesicle comprises a sterol. In some embodiments, the sterol is selected from the group consisting of cholesterol, fecosterol, sitosterol, ergosterol, campesterol, stigmasterol, brassicasterol, and mixtures thereof.

In some embodiments, the lipid vesicle comprises 1,2-dioleoyl-sn-glycero-3-phosphocholine (DOPC), 1,2-dioleoyl-sn-glycero-3-phosphoethanolamine (DOPE), sphingomyelin, and cholesterol. In some embodiments, the lipid vesicle comprises 1,2-dioleoyl-sn-glycero-3-phosphocholine (DOPC), 1,2-dioleoyl-sn-glycero-3-phosphoethanolamine (DOPE), sphingomyelin, and cholesterol, in a ratio of about 2:1:1:1, respectively.

In some embodiments, the lipid vesicle is from about 20 nm to about 400 nm in size.

In some embodiments, the transmembrane stem cell factor (tmSCF) polypeptide is human tmSCF, or a variant thereof. In some embodiments, the transmembrane stem cell factor (tmSCF) polypeptide comprises SEQ ID NO:1, or an amino acid sequence that is at least 65% identical to SEQ ID NO:1. In some embodiments, the transmembrane stem cell factor (tmSCF) polypeptide is a homologue of human tmSCF, or a variant thereof.

In some embodiments, the tmSCF protein comprises SEQ ID NO:1 [the protein of GenBank Accession No. NP_003985.2 (human tmSCF)], or a fragment or a variant thereof having at least about 65%, 70%, 75%, 80%, 85%, 86%, 87 88%, 89%, 90%, 91%, 92%, 93%, 94%, 95%, 96%, 97%, 98%, or 99% amino acid sequence identity. In addition to the human sequence for tmSCF, additional homologues from other species are known in the art and can also be used. Examples of additional tmSCF proteins include AAK92486.1 and NP_000890.1 (human isoforms). In some embodiments, the tmSCF protein (for example, comprising SEQ ID NO:1) comprises a His tag (for example, 6× His tag for purification).

In some embodiments, the transmembrane stem cell factor (tmSCF) polypeptide is encoded by the nucleic acid sequence SEQ ID NO:3, or a nucleic acid sequence that is at least 65% identical to SEQ ID NO:3. In some embodiments, the tmSCF protein is encoded by the nucleic acid sequence SEQ ID NO:3 [the coding sequence of GenBank Accession No. NM_003994 (human tmSCF)], or a fragment or a variant thereof having at least about 65%, 70%, 75%, 80%, 85%, 86%, 87 88%, 89%, 90%, 91%, 92%, 93%, 94%, 95%, 96%, 97%, 98%, or 99% amino acid sequence identity.

In some embodiments, the composition is encapsulated in a biodegradable microcapsule or microbead. In some embodiments, the microcapsule or microbead comprises a biocompatible hydrogel. In some embodiments, the biocompatible hydrogel comprises a polysaccharide. In some embodiments, the biocompatible hydrogel comprises alginate. In some embodiments, the microcapsule or microbead can comprise alginate gel, collagen gel, fibrin gel, poly (lactic-co-glycolic acid) (PLGA), or any mixture thereof. The microcapsules or microbeads can be any size suitable to encapsulate the tmSCF proteoliposomes or nanodiscs. For example, the microcapsules or microbeads can be from 1 μm in diameter, up to 3 mm in diameter, including about 1 μm to 100 μm, 100 μm to 1 mm, or 1 mm to 3 mm. The amount of tmSCF proteoliposomes or nanodiscs in the microcapsules or microbeads can be individually selected based upon release rates of the biodegradable microcapsules or microbeads, and requirements of the target tissue.

In some aspects, disclosed herein is a method for promoting angiogenesis in a subject, comprising administering to a subject in need thereof an effective amount of a composition comprising a transmembrane stem cell factor (tmSCF) polypeptide embedded in a lipid vesicle.

In some embodiments, the subject has been diagnosed with peripheral vascular disease (PVD), a chronic wound, an ischemic cardiovascular disorder, or a cerebrovascular disorder.

In some aspects, disclosed herein is a method for treating a subject with peripheral vascular disease (PVD), comprising administering to a subject in need thereof a therapeutically effective amount of a composition comprising a transmembrane stem cell factor (tmSCF) polypeptide embedded in a lipid vesicle.

In some aspects, disclosed herein is a method of treating acute coronary syndromes, stroke, peripheral vascular diseases, vascular complications in diabetic patients, or atherosclerosis comprising administering to a subject in need thereof a therapeutically effective amount of a composition comprising a transmembrane stem cell factor (tmSCF) polypeptide embedded in a lipid vesicle. In some embodiments, the peripheral vascular disease is peripheral ischemia.

In some aspects, disclosed herein is a method for expanding a hematopoietic stem cell population, the method comprising providing to the stem cell population a composition comprising a transmembrane stem cell factor (tmSCF) polypeptide embedded in a lipid vesicle, in an amount effective to expand the stem cell population.

As SCF is a hematopoietic growth factor that stimulates the bone marrow and native vasculature, there are many applications that can benefit from tmSCF therapies that do not suffer from the hyperreactivity response. In addition to treating peripheral ischemia, applications of this technology include preventing damage (healing the brain) following stroke, treating diabetic foot ulcers, and protecting hematopoietic cells during chemotherapy for cancer. As there has been great difficulty in culturing hematopoietic cells for their in vitro expansion, the compositions herein can be used as part of culture systems for hematopoietic cells for research or cell expansion for therapy.

In addition, myocardial ischemia caused by vascular disease in the coronary vessels of the heart is another highly prevalent condition that can benefit from this technology. Other applications include treating brain ischemia in stroke and enhancing wound closure for multiple types of injury.

Methods for preparing liposomes are found in the examples section below. Additional standard methods can be used, for example, as described in Das et al. (Das, et al. Overcoming disease-induced growth factor resistance in therapeutic angiogenesis using recombinant co-receptors delivered by a liposomal system. Biomaterials 35 (2014) 196e205). Briefly, standard lipid stock solutions are made for 10 mg/ml concentration in chloroform. In some embodiments, the following lipids are used: 1,2-dioleoyl-sn-glycero-3-phosphocholine (DOPC), 1,2-dioleoyl-sn-glycero-3-phosphoethanolamine (DOPE), cholesterol, and sphingomyelin (Avanti Polar Lipids) mixed in a ratio of 40:20:20:20 by volume, respectively. The solution mixture is prepared in a round-bottom flask, and the solvent is removed first using a Rotatory Evaporator (Heidolph Collegiate) for 1 h and then under a stream of argon gas for 15 min. The lipids are resuspended in a Hepes-buffered salt solution (10.0 mM Hepes and 150 mM NaCl in PBS, pH 7.4) by mixing, sonicating, and freeze-thawing to achieve a final solution of 13.2 mM total lipid. The final lipid solution is then extruded through a 400 nm polycarbonate membrane (Avestin). A detergent, 1% n-octyl-b-D-glucopyranoside (OG), is added. The concentration of the solution was reduced to 40% of the original in 10% increments every 30 min through dilution with PBS. The detergent and free protein was removed by extensive dialysis in PBS at 4° C. Residual OG was removed by repeated BioBead treatments (SM-2; Bio-Rad).

Transmembrane Stem Cell Factor (tmSCF) Nanodiscs

Nanodiscs (NDs) are made of a lipid bilayer where the lipids are surrounded by a membrane scaffold protein. NDs (comprising tmSCF) have spherical shape and their size is generally about 100-300 nm. In some embodiments, the NDs comprise POPC. The functional protein, tmSCF, is inserted in the lipid bilayer. Surrounded by the lipid bilayer, they are not only protected from enzymatic activity and aggregation, but also have greater activity since their environment is close to their native one.

In some aspects, disclosed herein is a composition comprising: a membrane scaffold protein; a lipid; and a transmembrane stem cell factor (tmSCF) polypeptide.

In some embodiments, the lipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, phosphatidyl choline (PC); phosphatidyl ethanolamine (PE), phosphatidyl inositol (PI); dihexanoyl phosphatidyl choline (DHPC), dipalmitoyl phosphatidyl ethanolamine, dipalmitoyl phosphatidyl inositol; dimyristoyl phosphatidyl ethanolamine; dimyristoyl phosphatidyl inositol; dihexanoyl phosphatidyl ethanolamine; dihexanoyl phosphatidyl inositol; 1-palmitoyl-2-oleoyl-phosphatidyl ethanolamine; 1-palmitoyl-2-oleoyl-phosphatidyl inositol, and mixtures thereof. In some embodiments, the lipid comprises 1-palmitoyl-2-oleoyl-sn-glycero-3-phosphocholine (POPC).

In some embodiments, the membrane scaffold protein to lipid weight ratio is about 1:65 and the size of the nanodisc range from 10 nm to 400 nm in size.

In some embodiments, the transmembrane stem cell factor (tmSCF) polypeptide is human tmSCF, or a variant thereof. In some embodiments, the transmembrane stem cell factor (tmSCF) polypeptide comprises SEQ ID NO:1, or an amino acid sequence that is at least 65% identical to SEQ ID NO:1. In some embodiments, the transmembrane stem cell factor (tmSCF) polypeptide is a homologue of human tmSCF, or a variant thereof.

In some embodiments, the tmSCF protein comprises SEQ ID NO:1 [the protein of GenBank Accession No. NP_003985.2 (human tmSCF)], or a variant thereof having at least about 65%, 70%, 75%, 80%, 85%, 86%, 87 88%, 89%, 90%, 91%, 92%, 93%, 94%, 95%, 96%, 97%, 98%, or 99% amino acid sequence identity. In addition to the human sequence for tmSCF, additional homologues from other species can also be used. In some embodiments, the tmSCF protein (for example, comprising SEQ ID NO:1) comprises a His tag (for example, 6× His tag for purification).

In some embodiments, the composition is encapsulated in a biodegradable microcapsule or microbead. In some embodiments, the microcapsule or microbead comprises a biocompatible hydrogel. In some embodiments, the biocompatible hydrogel comprises a polysaccharide. In some embodiments, the biocompatible hydrogel comprises alginate. In some embodiments, the microcapsule or microbead can comprise alginate gel, collagen gel, fibrin gel, poly(lactic-co-glycolic acid) (PLGA), or any mixture thereof. The microcapsules or microbeads can be any size suitable to encapsulate the tmSCF proteoliposomes or nanodiscs. For example, the microcapsules or microbeads can be from 1 μm in diameter, up to 3 mm in diameter, including about 1 μm to 100 μm, 100 μm to 1 mm, or 1 mm to 3 mm. The amount of tmSCF proteoliposomes or nanodiscs in the microcapsules or microbeads can be individually selected based upon release rates of the biodegradable microcapsules or microbeads, and requirements of the target tissue.

In some aspects, disclosed herein is a method for promoting angiogenesis in a subject, comprising administering to a subject in need thereof an effective amount of a composition comprising: a membrane scaffold protein; a lipid; and a transmembrane stem cell factor (tmSCF) polypeptide.

In some embodiments, the subject has been diagnosed with peripheral vascular disease (PVD), a chronic wound, an ischemic cardiovascular disorder, or a cerebrovascular disorder.

In some aspects, disclosed herein is a method for treating a subject with peripheral vascular disease (PVD), comprising administering to a subject in need thereof a therapeutically effective amount of a composition comprising: a membrane scaffold protein; a lipid; and a transmembrane stem cell factor (tmSCF) polypeptide.

In some aspects, disclosed herein is a method of treating acute coronary syndromes, stroke, peripheral vascular diseases, vascular complications in diabetic patients, or atherosclerosis comprising administering to a subject in need thereof a therapeutically effective amount of a composition comprising: a membrane scaffold protein; a lipid; and a transmembrane stem cell factor (tmSCF) polypeptide. In some embodiments, the peripheral vascular disease is peripheral ischemia.

In some aspects, disclosed herein is a method for expanding a hematopoietic stem cell population, the method comprising providing to the stem cell population a composition comprising a membrane scaffold protein, a lipid, and a transmembrane stem cell factor (tmSCF) polypeptide, in an amount effective to expand the stem cell population.

Nanodisc technology, and examples of membrane scaffold proteins, are known in the art and are described in, for example, U.S. Pat. Nos. 7,691,414; 7,662,410; 7,622,437; 7,592,008; 7,575,763; 7,083,958; 7,048,949, each of which are hereby incorporated by reference in their entirety. In some embodiments, the membrane scaffold protein is 1D1 (commercially available from Sigma Aldrich). In some embodiments, the membrane scaffold protein comprises SEQ ID NO:4, or a sequence that is at least 65% identical to SEQ ID NO:4. In some embodiments, membrane scaffold protein comprises SEQ ID NO:4, or a fragment or a variant thereof having at least about 65%, 70%, 75%, 80%, 85%, 86%, 87 88%, 89%, 90%, 91%, 92%, 93%, 94%, 95%, 96%, 97%, 98%, or 99% amino acid sequence identity.

Compositions

Compositions, as described herein, comprising a tmSCF proteoliposome (or a tmSCF nanodisc) and an excipient of some sort may be useful in a variety of applications as described herein.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, varoius gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1

Figure 2:
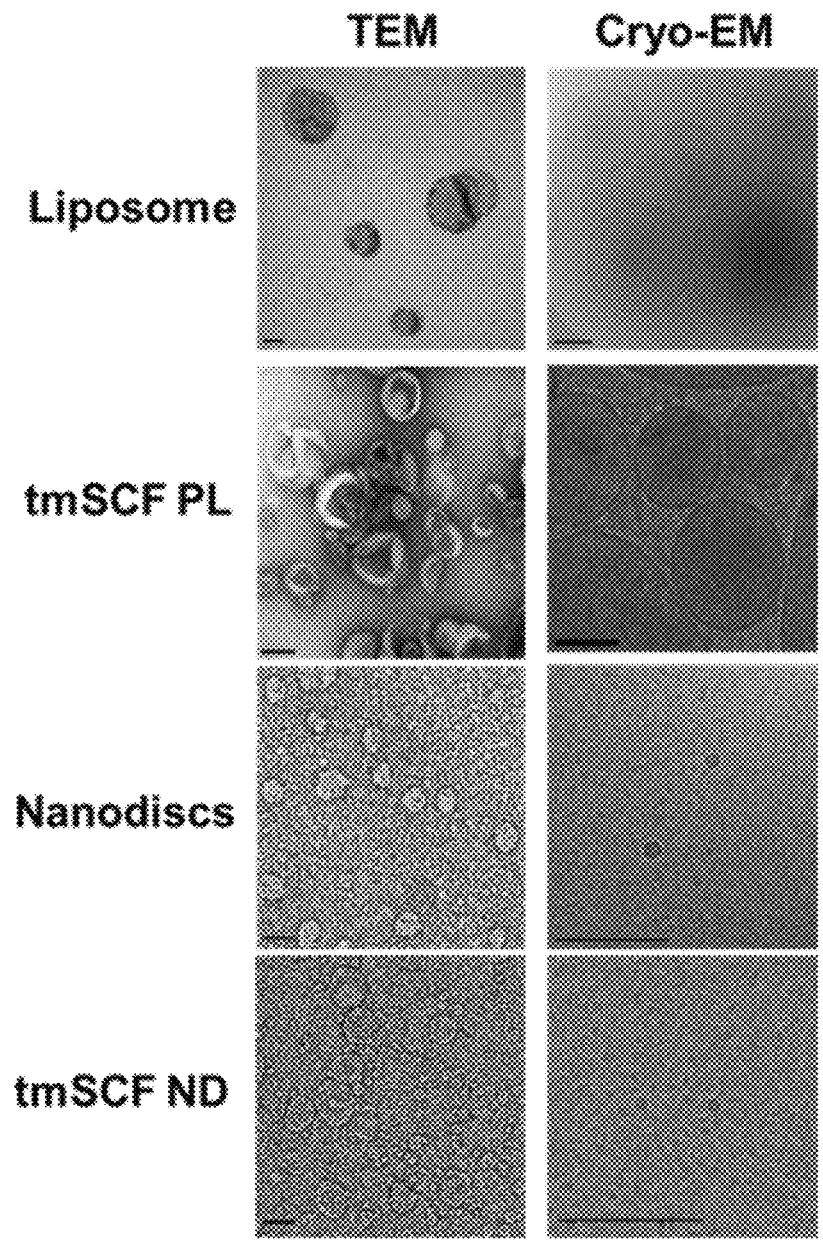
Figure 8:
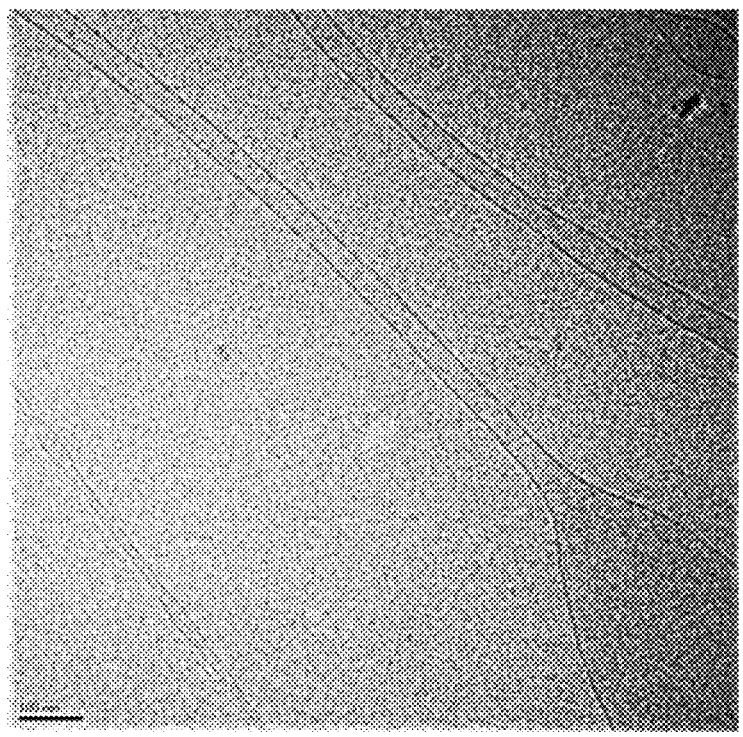
FIG. 8. Cryo-EM image of tmSCFPL. Tubelation was confirmed. Size scale 100 nm.

Transmembrane Stem Cell Factor (tmSCF) with Lipid Carrier as Protein Therapy for Peripheral Vascular Disease
Fabrication of Proteoliposomes and Nanodiscs with tmSCF Transmembrane stem cell factor (tmSCF) protein was first harvested and purified as described in the methods section below. SDS-PAGE and silver staining were performed to analyze the purity of the final concentrated samples. As shown in FIGS. 1A and B, the results of silver staining and western blotting indicate the high purity of tmSCF protein. tmSCF proteoliposomes (tmSCFPLs) were then fabricated by combining detergent solubilized tmSCF and empty liposome, followed by serial dilution and dialysis. The size of the empty liposomes and tmSCF were measured by dynamic light scattering (DLS) as shown in FIG. 1C. The size of empty liposome and tmSCFPLs were confirmed to be around 300 nm and 400 nm, respectively. The shape of tmSCFPLs was also revealed by TEM and cryo-TEM shown in FIG. 2. Interestingly, tubulation was also confirmed on many tmSCFPLs (FIG. 8), which indicates that tmSCF was actually inserted on the surface of the liposome. tmSCF nanodiscs (tmSCF NDs) were also fabricated by combining detergent solubilized tmSCF and empty nanodiscs, followed by dialysis. DLS confirmed the size of empty nandiscs to be 20-30 nm, and tmSCF NDs to be around 150 nm (FIG. 1D). Some disc like shape is also seen in TEM and cryo-EM images shown in FIG. 2. tmSCF concentration in tmSCFPLs and tmSCFNDs were determined 55 µg/ml and 77 µg/ml, respectively.

Tube Formation Assay

Figure 3:
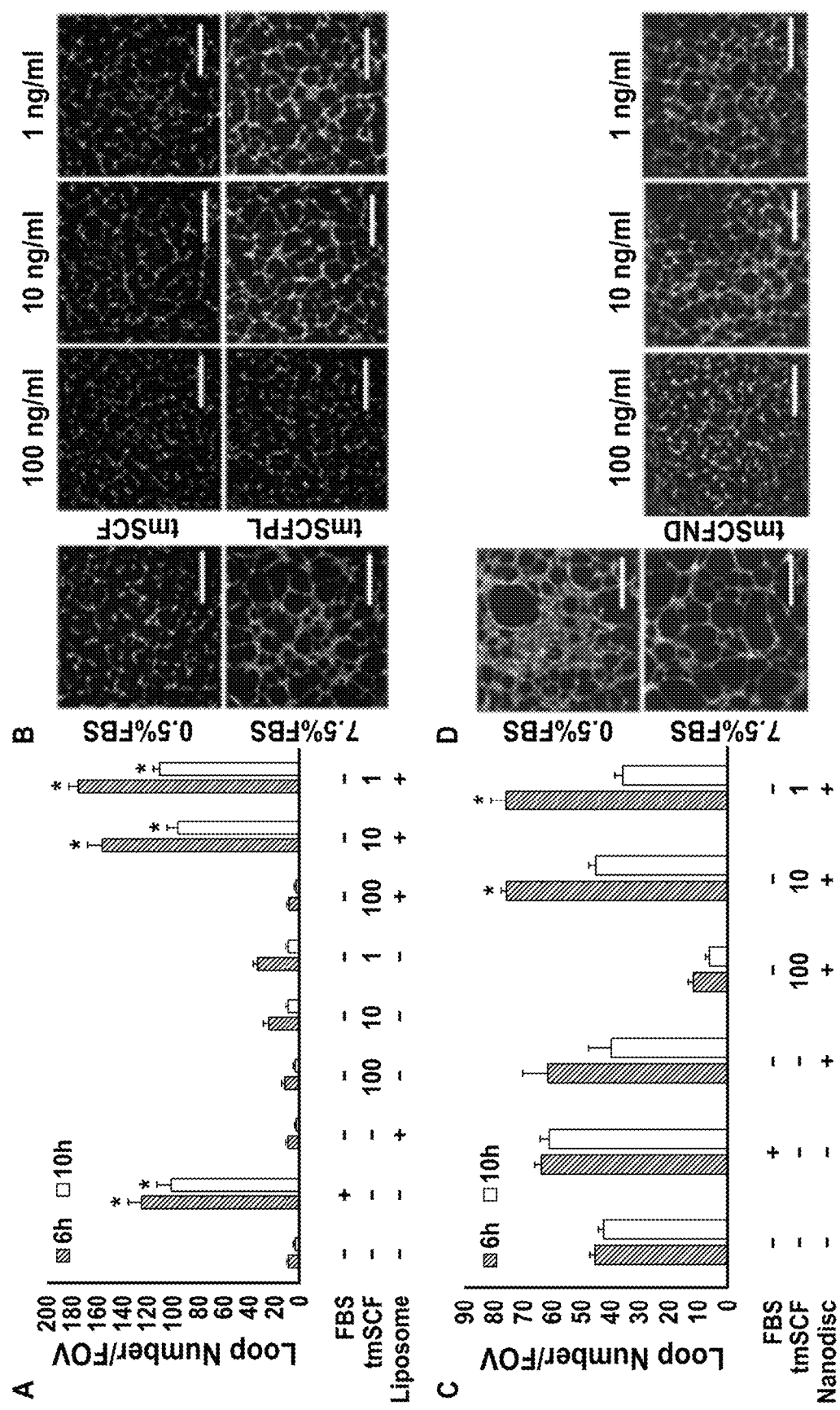
FIG. 3. Characterization of tmSCF liposome and nanodisc effects on loop number and blood flow recovery. (A) Loop number after 6 h and 10 h of treatments. tmSCF protein concentration is in ng/ml. * indicates significant difference ($P<0.05$) over 0.5% FBS. FBS negative=0.5% serum. FBS positive=7.5% serum. (B) Representative pictures of tube formation. Sale bar=300 µm. (C) Relative blood flow recovery (%) of the ischemic versus control limb. * indicates significant difference ($P<0.05$) on tmSCFPL over alginate. (D) Representative pictures of mice feet at day 14.
Figure 9:
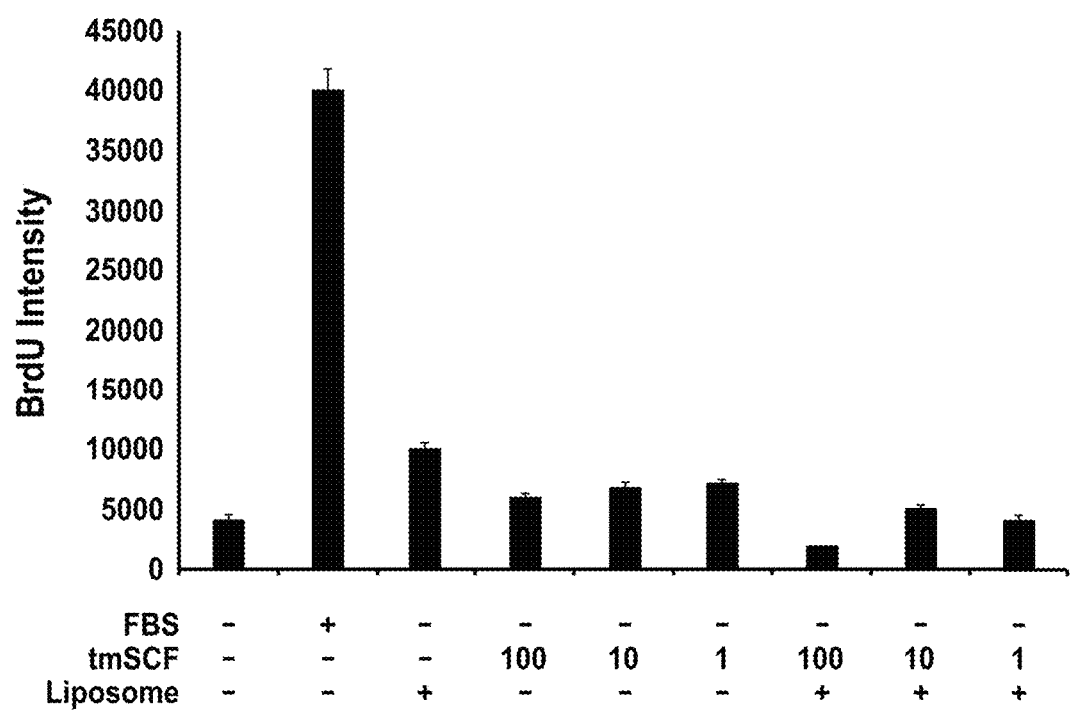
FIG. 9. Proliferation assay on tmSCFPL treated HUVEC. FBS negative=0.5% serum. FBS positive=7.5% serum.
Figure 10:
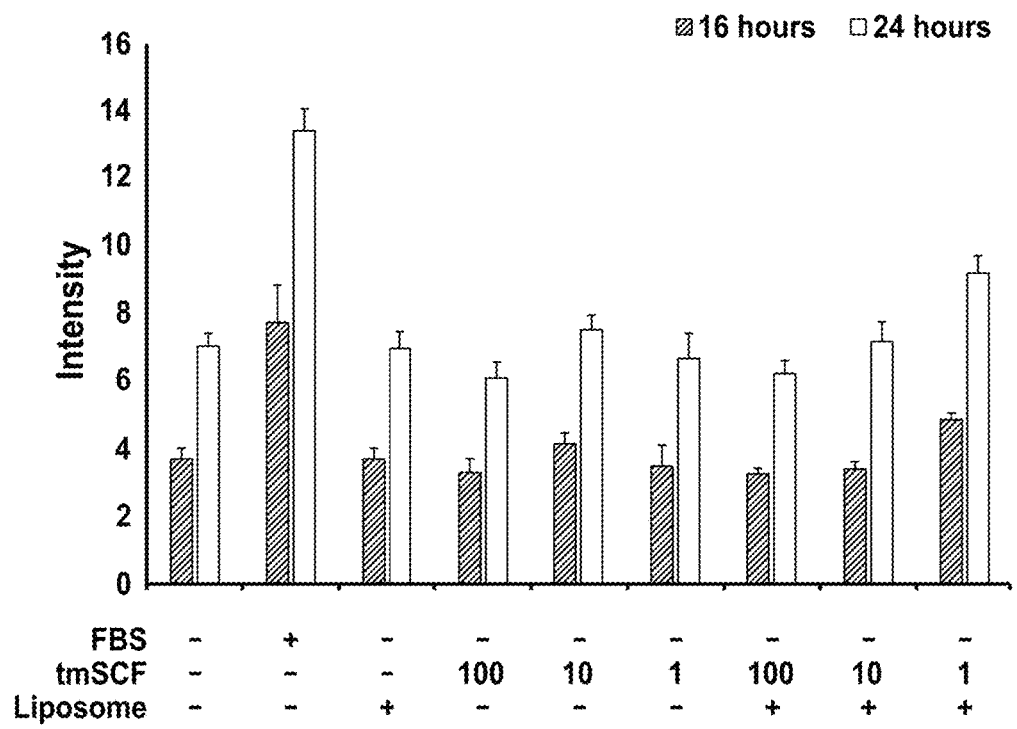
FIG. 10. Migration assay result on tmSCFPL treated HUVEC. FBS negative=0.5% serum. FBS positive=7.5% serum.

To measure the angiogenic ability of tmSCFPLs and NDs, a tube formation assay on HUVEC was performed. Twenty-four hours before the treatments, cells were starved in serum-depleted media. Treatments include three kinds of concentration (1 ng/ml, 10 ng/ml, and 100 ng/ml) of tmSCF for protein itself, PLs and NDs. Loop number was measured as an angiogenic parameter. Interestingly, tmSCF protein itself did not have a strong tube formation ability, but PLs showed 16-18 fold higher activity (FIGS. 3A and 3B) Similar results were seen in NDs treatment (FIGS. 3C and D). Proliferation and migration assays were also performed on HUVEC to see whether or not tmSCF nanocarriers support proliferation and migration. As shown in FIG. 9 and FIG. 10, tmSCF nanocarriers do not support proliferation or migration of HUVEC.

Protein Uptake Kinetics

Figure 4:
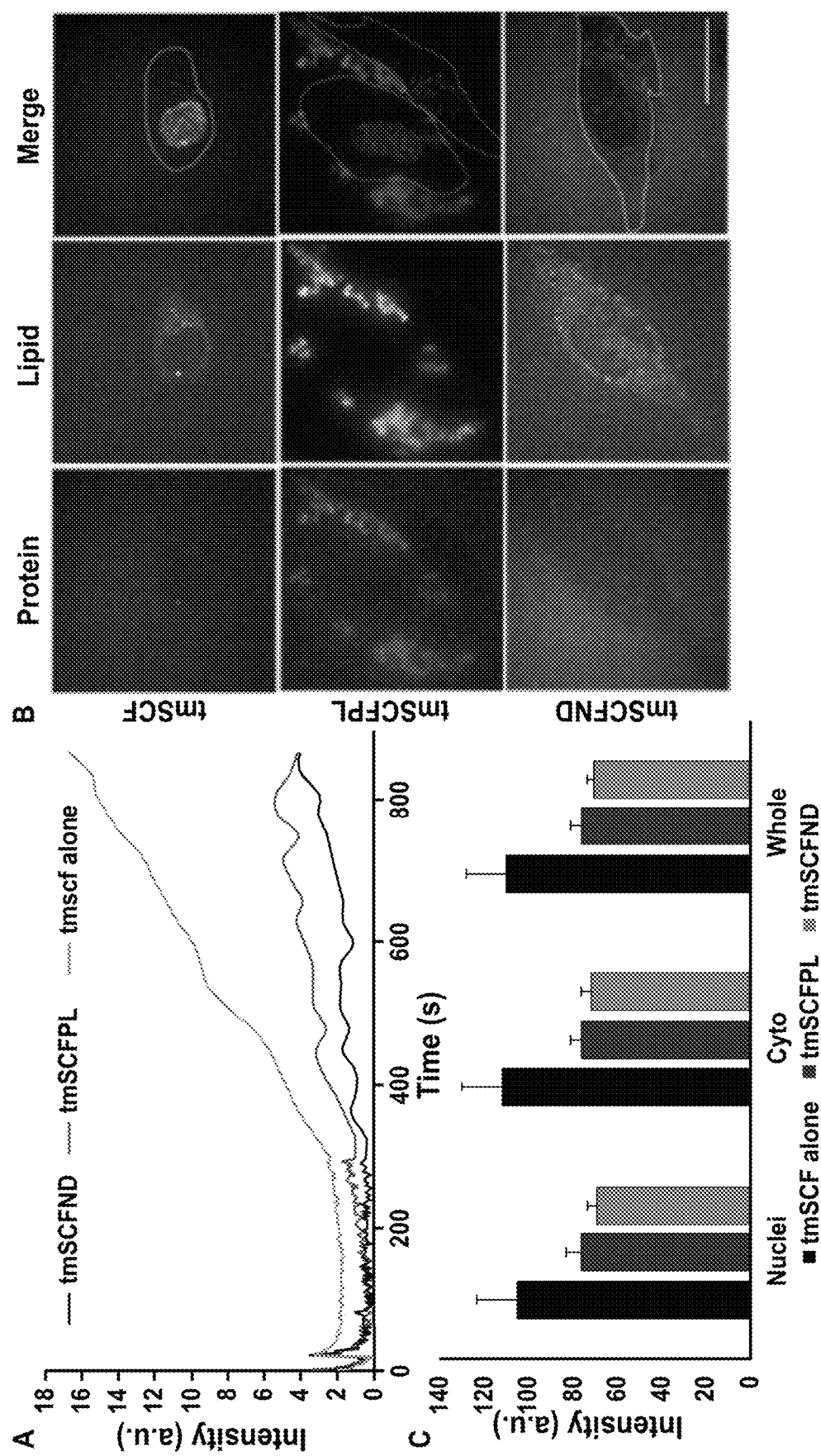
FIG. 4. Characterization of protein uptake of tmSCF liposomes and nanodiscs. (A) tmSCF protein uptake kinetics over time. (B) tmSCF Protein and lipid localization images at time 15 minutes. (C) tmSCF protein intensity at time 15 minutes. Intensity was measured in nuclei, cytoplasm and whole cell.

Protein uptake kinetics were observed by fluorescent live imaging. Here, tmSCF protein conjugated with a fluorescent dye Alexa 594, and green fluorescent lipid was used to stain nanocarriers. Protein concentration was adjusted to the same in every treatment groups. FIG. 4A shows time dependent protein intensity change inside of cells. This indicates that protein uptake is much faster if protein was added alone. Nanocarriers seem to slow down the protein uptake speed. After 15 minutes, more protein was uptaken by tmSCF protein alone compared to tmSCFPLs or NDs (FIG. 4C). Another interesting result is seen in FIG. 4B. After 15 minutes of incubation, a large amount of green fluorescence was observed inside of cells in NDs, but not in PLs, indicating that nanocarriers are internalized by cells for ND treatment, but not for PLs.

Hind Limb Ischemia on WT and ob/ob Mice

Figure 5:
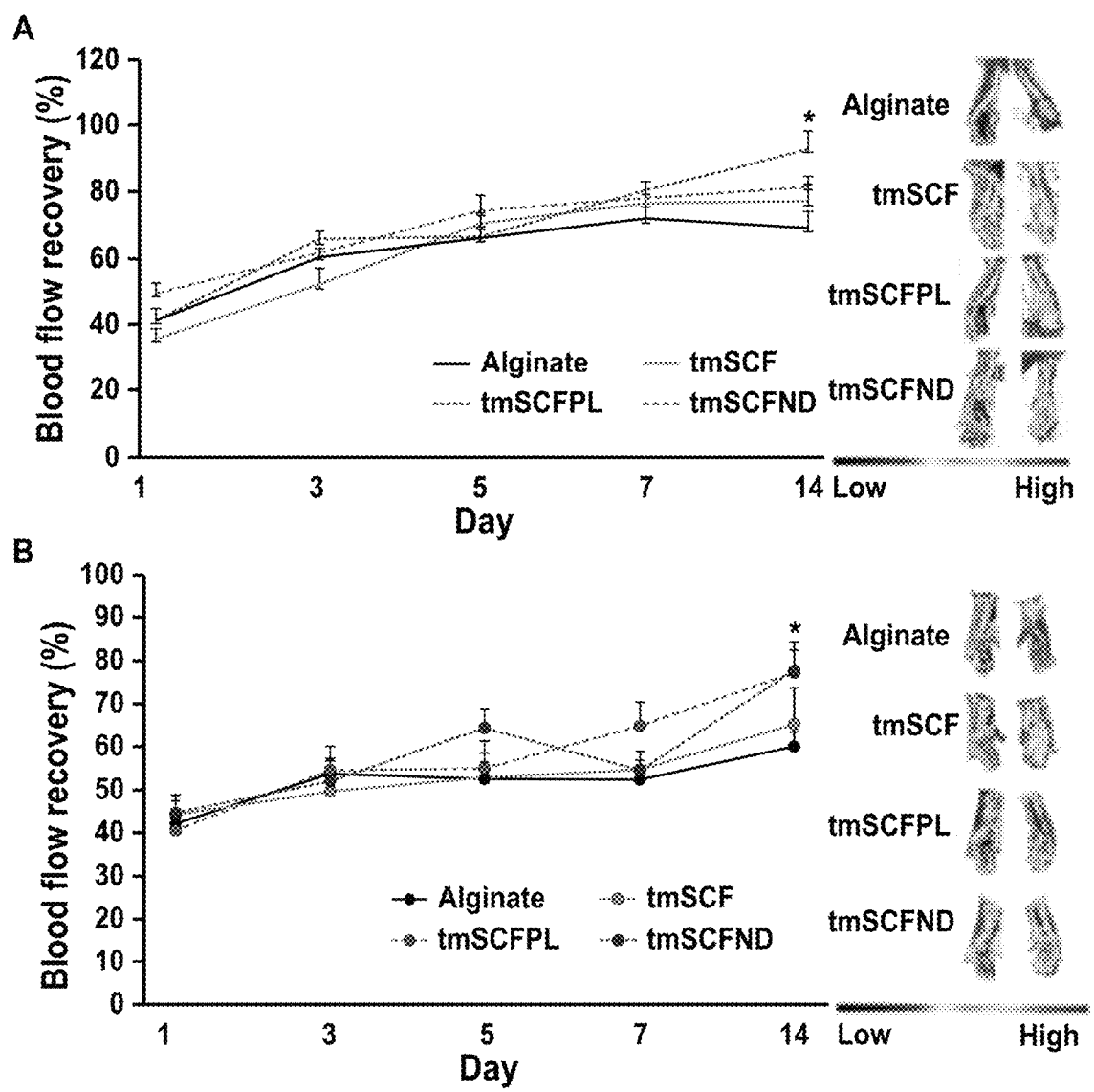
FIG. 5. Blood flow recovery in wild type mice treated with tmSCF liposomes and nanodiscs. (A) Relative blood flow recovery over time on WT mice, and representative picture of mice foot at Day 14. * indicates significant difference (P<0.05) over alginate group. (B) Relative blood flow recovery over time on ob/ob mice, and representative picture of mice foot at Day 14. * indicates significant difference (P<0.05) over alginate group.

To measure the angiogenic potential of tmSCFPLs and NDs in vivo, hind limb ischemia model was performed on WT mice. Ten-week old male mice were used for this study. Treatments were encapsulated in 2% alginate gel, and cross-linked in $CaCl_2$ solution for 1 hour. After femoral artery was ligated, alginate encapsulated treatments were placed at ischemic site. Incision was closed by sutured, and blood flow recovery was recorded by laser speckle imaging over 14 days. FIG. 5A shows relative blood flow recovery graph and representative pictures at Day 14 mice feet. Left foot is contralateral control (no surgery), and right foot is ischemic foot. Relative blood flow was calculated by dividing ischemic foot blood flow by contralateral control foot. FIG. 5A shows significantly higher relative blood flow in tmSCFPLs group compared to the alginate group, indicating effective treatment of tmSCFPLs. FIG. 5B shows the results of hind limb ischemia model on ob/ob mice. At Day 14, significantly higher blood flow recoveries were seen in tmSCFPLs and tmSCFNDs compared to alginate only control.

Histology on Wild Type and ob/ob Mice with Hind Limb Ischemia

Figure 6:
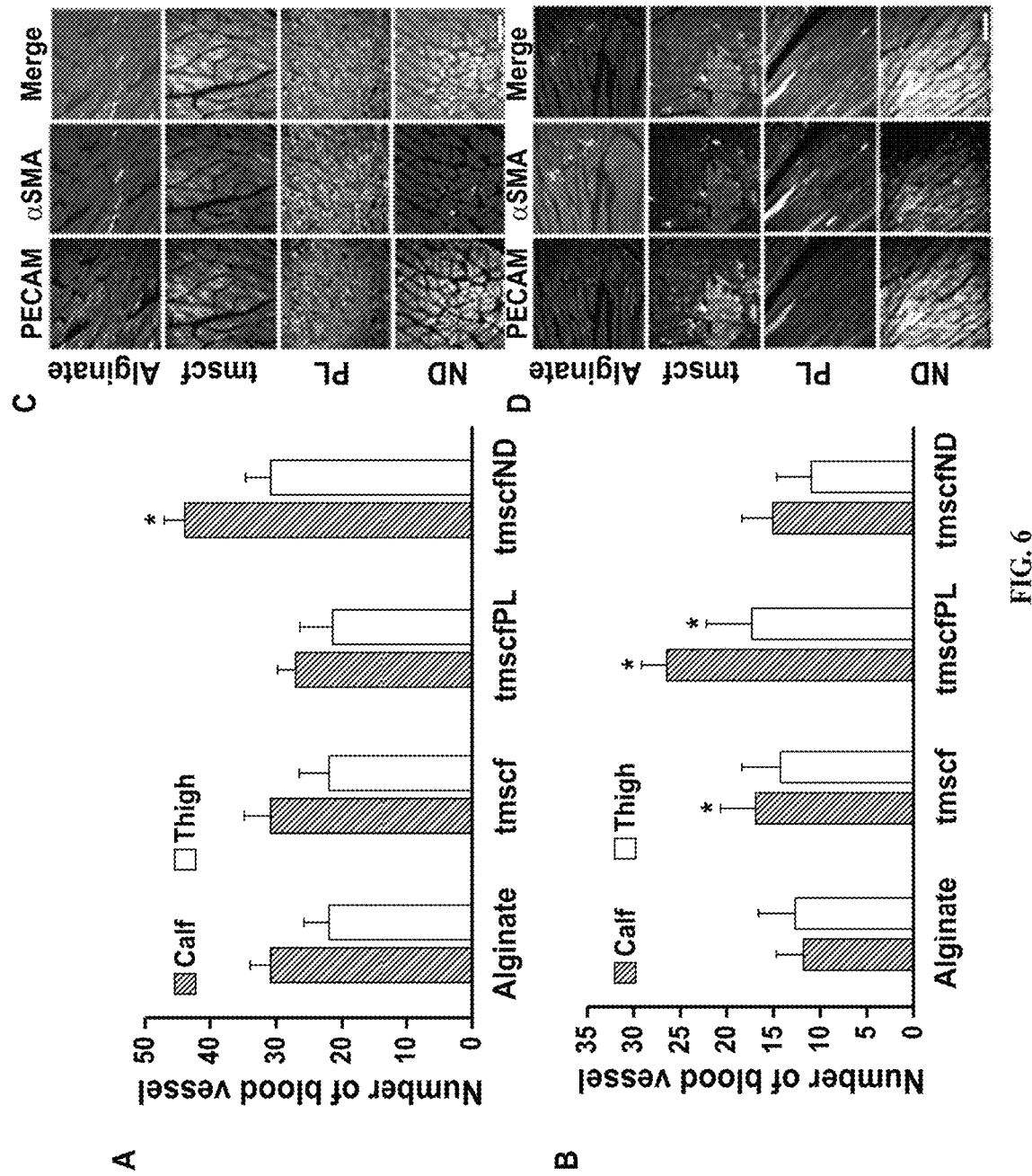
FIG. 6. Quantification of small and mature blood vessels in wild type mice treated with tmSCF liposomes and nanodiscs. (A) Quantification of small blood vessels on thigh and calf muscle harvested at Day 14 on WT mice. *p<0.05 versus alginate. (B) Quantification of matured blood vessels on thigh and calf muscle harvested at Day 14 on WT mice. *p<0.05 versus alginate. (C) Immunostaining of PECAM, αSMA on calf muscle of WT mice. Scale bar 300 µm. (D) Immunostaining of PECAM, αSMA on thigh muscle of WT mice. Scale bar 300 µm.
Figure 7:
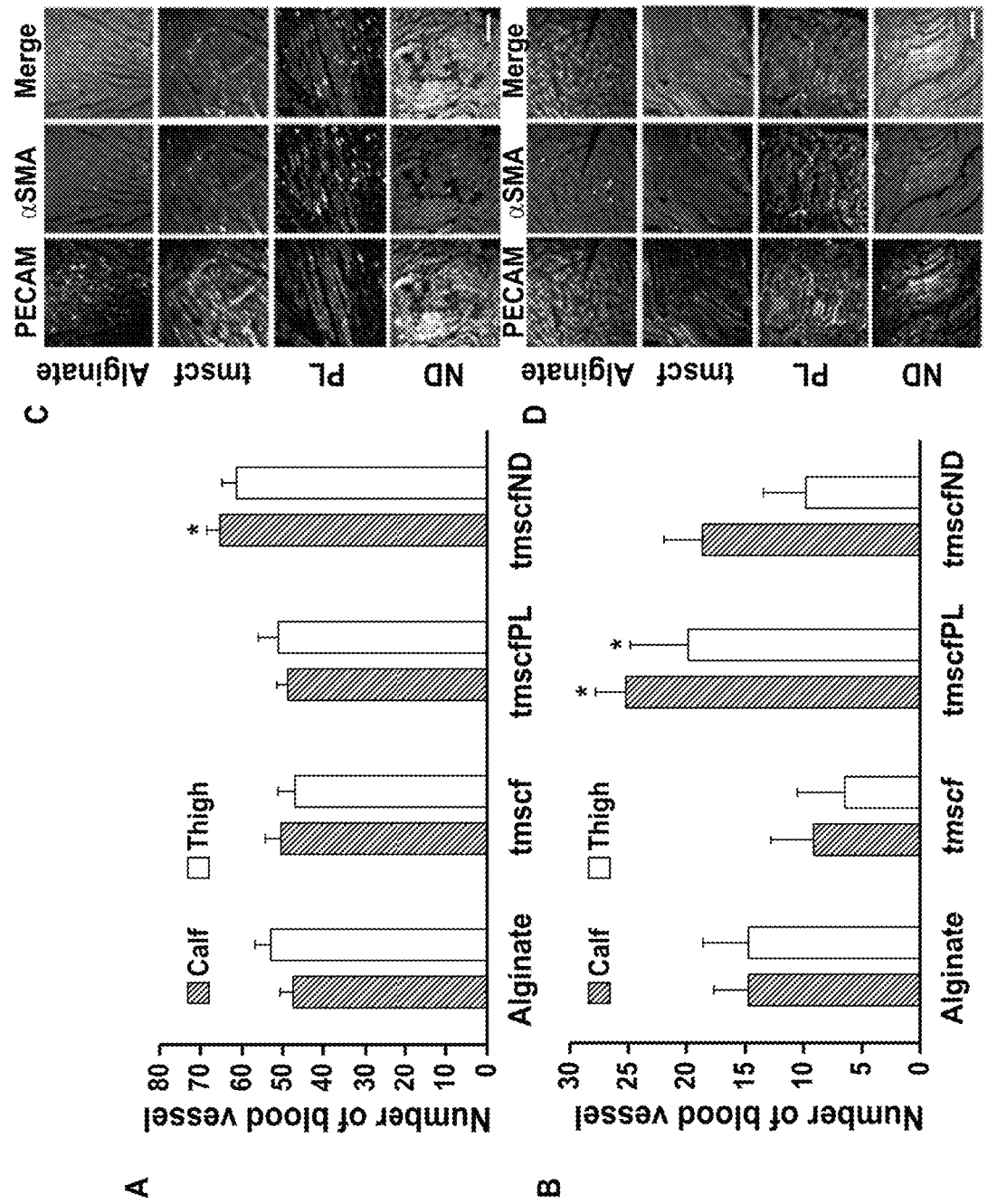
FIG. 7. Quantification of small and mature blood vessels in ob/ob mice treated with tmSCF liposomes and nanodiscs. (A) Quantification of small blood vessels on thigh and calf muscle harvested at Day 14 on ob/ob mice. *p<0.05 versus alginate. (B) Quantification of matured blood vessels on thigh and calf muscle harvested at Day 14 on ob/ob mice. *p<0.05 versus alginate. (C) Immunostaining of PECAM, αSMA on calf muscle of ob/ob mice. Scale bar 300 µm. (D) Immunostaining of PECAM, αSMA on thigh muscle of ob/ob mice. Scale bar 300 µm.
Figure 11:
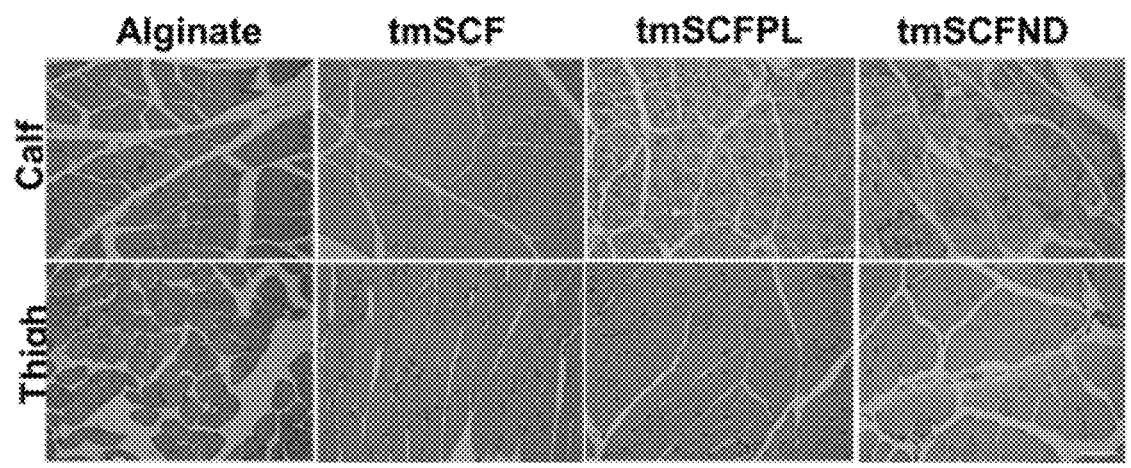
FIG. 11. H&E staining on WT mice. Scale bar is 500 µm.
Figure 12:
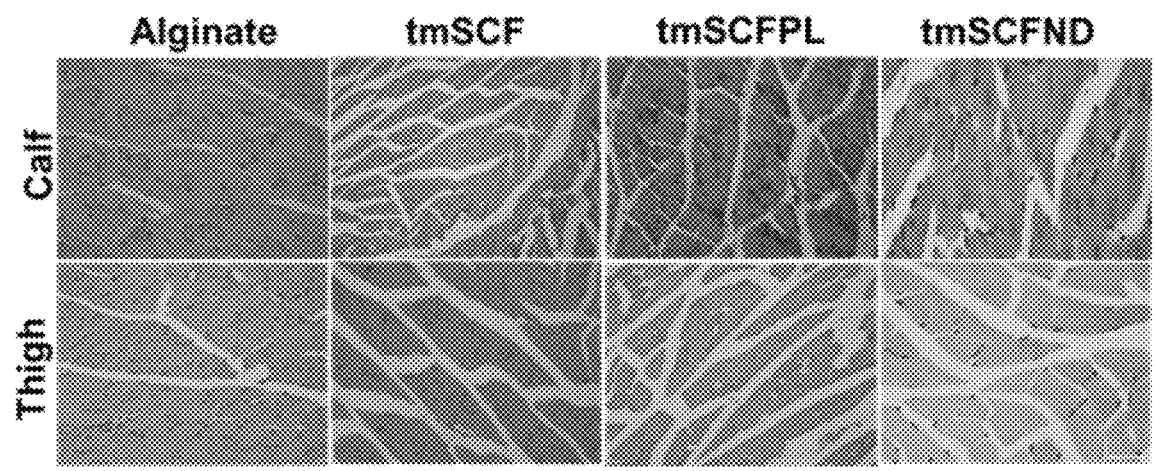
FIG. 12. H&E staining on ob/ob mice. Scale bar is 500 µm.

First, H&E staining of WT and ob/ob mice muscles did not show any defects or abnormal features (FIG. 11 and FIG. 12). Immunohistochemical staining on WT for endothelial cells (PECAM-1) and smooth muscle cells (αSMA) revealed interesting trends happening under tmSCFPLs and NDs treatment. The staining was done on the harvested thigh and calf muscles at Day 14, and representative pictures are shown in FIGS. 6C and 6D. FIG. 6A shows the quantification results of the number of small blood vessels counted by PECAM staining. As seen in this graph, a significantly higher amount of small blood vessels was formed at Day 14 under tmSCFNDs treatment. On the other hand, the higher number of matured blood vessels (αSMA staining) was seen in tmSCFPLs treated groups (FIG. 6B). These results indicate that tmSCFPLs may facilitate the blood flow recovery faster than NDs. Similar tendency was observed in ob/ob mice as shown in FIG. 7A-D.

Methods

Preparation of tmSCF Proteoliposomes:

For the production of recombinant tmSCF, HEK-293Ta cells were transduced with lentiviral vector with constitutive expression of 6× His tagged tmSCF. Viruses were produced in HEK-293Ta cells using human lentiviral packaging system according to the manufacturer's instructions (Genecopoeia). Puromycin was used to select only for transduced cells. The cells were lysed in a buffer containing 20 mM Tris (pH 8.0), 150 mM NaCl, 1% Triton X-100, 2 mM sodium orthovanadate, 2 mM PMSF, 50 mM NaF, and protease inhibitors (Roche) at room temperature. TmSCF was then isolated using cobalt chelating column (Chelating column; GH Heakthcare), and the buffer was exchanged in 1×PBS. After concentrating the protein solution with Centriprep concentrators (Millipore), the final working concentration of protein was found to be 12 ng/ml using a BCA Protein Assay kit (Thermo Scientific). Purity of the protein was confirmed by SDS-PAGE followed silver staining of the gel. To prepare liposomes, stock solutions (10 mg $mL^{-1}$) of 1,2-dioleoyl-sn-glycero-3-phosphocholine, 1,2-dioleoyl-sn-glycero-3-phosphoethanolamine, cholesterol, and sphingomyelin were prepared in chloroform. The lipids were mixed in the volumetric ratio 2:1:1:1 in a round bottom flask and the chloroform was removed on rotatory evaporator attached to a vacuum pump. Liposomes were resuspended in 4-(2-hydroxyethyl)-1-piperazineethanesulfonic acid buffer by vortexing, sonication, and freeze thawing. Extruding device (Avanti Polar Lipids) with polycarbonate membranes (400 nm) was used to homogenize the liposome population. A mild detergent, n-octyl-β-D-glucopyranoside (1% w/v) was added to both the liposome and the recombinant tmSCF. The protein and liposomes were then combined and the detergent was removed by timed serial dilution (every 30 min, 10% dilution up to 2 h), dialysis, and treatment with Biobeads (Biorad).

Preparation of tmSCF Nanodiscs:

As a lipid source, 1-palmitoyl-2-oleoyl-sn-glycero-3-phosphocholine (POPC) was used in this study. POPC was stored in chloroform, so chloroform was first removed by rotary evaporator. After that, POPC was resuspended in sodium cholate (100 mM). MSP protein was then added to phospholipid solution, and the detergent concentration was adjusted between 14-40 mM. This construct was incubated for 15 minutes at 4° C. To solubilize the membrane protein, tmSCF was incubated in the n-octyl-β-D-glucopyranoside (1% w/v) for 15 minutes at 4° C. After 15 minutes incubation of lipid construct and tmSCF protein, these were combined and incubated for 1 hour at 4° C. Final detergent concentration was adjusted to 20 mM with sodium cholate. Finally, detergent was removed by dialysis and biobeads.

tmSCF Nanocarriers Characterization:

The size and dispersion of the proteoliposomes were characterized by dynamic light scattering (Malvern Zetasizer Nano ZS). Calibration was performed using 54 nm polystyrene particles. For TEM imaging of proteoliposomes, carbon support grids (300 mesh Cu; EM Sciences) were treated with glow discharge at 50 mA for two minutes (Emitech K100X; Quorum Technologies). The samples were then applied to the grids and the excess liquid removed with a filter paper. 2% uranyl acetate solution was used to stain glids, and images were taken using an FEI Tecnai Transmission Electron Microscope (TEM). For cryo-electron microscopy imaging, the liposomes were plunge-frozen in liquid ethane on carbon holey film grids (R2X2 Quantifoil; Micro Tools GmbH, Jena, Germany) The grids were transferred to a cryo-specimen holder (Gatan 626) under liquid nitrogen and put in a microscope (JEOL 2100 LaB6, 200 keV), Grids were maintained at close to liquid nitrogen temperature during EM session (−172° C.-180° C.).

Tube Formation Assay:

Cells were stained with cell tracker green, cultured and starved 24 h prior to the experiment. Growth factor reduced matrigel (Corning) was coated on the 96 well plate, and endothelial cells were seeded on top of it with seeding density of $4 \times 10^4$/well. Treatments were then added and cells incubated for 6 h and 10 h. Images were taken by citation 5 at each time points, and the number of loops was quantified.

Cell Proliferation Assay:

Endothelial cells were passaged into a 96-well plate and cultured in low serum media with 2% FBS for 24 h. Treatments were then added to cells. After 24 h, BrdU was added to the cells and proliferation was assessed 12 h later using a colorimetric BrdU assay (Cell Signaling, Inc.).

Cell Migration Assay:

Endothelial cells were stained with cell tracker green, and passaged to confluence in 96-well migration assay kit (Platypus). Treatments were added for 24 h before assay starts. A cell stopper was then removed to allow cells to migrate. Migration area and green fluorescent intensity were read by citation 5 after 16 h and 24 h.

Protein Uptake Study:

Proteins were labeled with Alexa Fluor 594 (Thermo Scientific) and liposome was labeled green by adding 0.3 mol % of 1-Oleoyl-2-[12-[(7-nitro-2-1,3-benzoxadiazol-4-yl)amino]dodecanoyl]-sn-Glycero-3-Phosphocholine (Avanti). Proteoliposomes were fabricated by mixing these fluorescently tagged proteins and liposome. For live imaging, endothelial cells were cultured to 70% confluent and stained with DAPI before the treatments. Right after the treatments were added, images were taken every 30 seconds for 15 min by confocal microscopy. Intensity inside of the cells were measured by image J and photoshop.

Hind Limb Ischemia Model:

Prior to surgery, treatment encapsulated alginate beads were fabricated. 2% sodium alginate solution and treatment were mixed. 30 G needle was used to create alginate beads which was dropped into the 1.1% calcium chloride solution to crosslink for 1 hour. Wild-type mice and ob/ob mice were used in the studies. To perform the hind limb ischemia studies, mice were anesthetized with 2-3% isoflurane gas and a longitudinal incision was made in the inguinal region of the right thigh. The femoral artery was separated from the femoral vein and nerve, and then double ligated with 6-0 silk sutures at two locations and the artery severed at each ligation. Treatments were then implanted in the pocket created by the surgery.

Immunohistochemistry:

Thigh and calf muscles were formalin fixed and embedded in paraffin following standard procedures prior to sectioning. The sections were deparaffinized and treated for 3 hours with antigen retrieval solution (Dako) at 80° C. The sections were cooled to room temperature and blocked with 20% fetal bovine serum for 45 minutes and then immunostained overnight with 1:100 dilution of primary antibody to PECAM-1 (Cell Signaling) and a 1:100 dilution of primary antibody to αSMA (abcam). Secondary staining was performed by with antibodies conjugated to alexa594 or alexa488. Following staining, the samples were imaged using confocal microscopy. Following immunostaining for PECAM-1, the number of small vessels was counted in images from each of the mice Staining for αSMA in combination with PECAM-1 was used for counting the number of mature blood vessels.

Statistical Analysis:

All results are shown as mean±standard error of the mean. Comparisons between only two groups were performed using a 2-tailed Student's t-test. Differences were considered significant at $p<0.05$. Multiple comparisons between groups were analyzed by 2-way ANOVA followed by a Tukey post-hoc test. A 2-tailed probability value $<0.05$ was considered statistically significant.

SEQUENCES

Human tmSCF protein coding sequence (NP_003985.2) (SEQ ID NO: 1)

```
  1    mkktqtwilt ciylqlllfn plvktegicr nrvtnnvkdv tklvanlpkd ymitlkyvpg 61    mdvlpshcwi semvvqlsds ltdlldkfsn iseglsnysi idklvnivdd lvecvkenss 121    kdlkksfksp eprlftpeef frifnrsida fkdfvvaset sdcvvsstls pekgkaknpp 181    gdsslhwaam alpalfslii gfafgalywk krqpsltrav eniqineedn eismlqeker 241    efqev
```

Human tmSCF mRNA sequence (NM_003994) (SEQ ID NO: 2)

```
  1    gggcttcgct cgccgcctcg cgccgagact agaagcgctg cgggaagcag ggacagtgga 61    gagggcgctg cgctcgggct acccaatgcg tggactatct gccgccgctg ttcgtgcaat 121    atgctggagc tccagaacag ctaaacggag tcgccacacc actgtttgtg ctggatcgca
```

| | SEQUENCES |
|---|---|
| 181 | gcgctgcctt tccttatgaa gaagacacaa acttggattc tcacttgcat ttatcttcag |
| 241 | ctgctcctat ttaatcctct cgtcaaaact gaagggatct gcaggaatcg tgtgactaat |
| 301 | aatgtaaaag acgtcactaa attggtggca aatcttccaa aagactacat gataaccctc |
| 361 | aaatatgtcc ccgggatgga tgttttgcca agtcattgtt ggataagcga gatggtagta |
| 421 | caattgtcag acagcttgac tgatcttctg dacaagtttt caaatatttc tgaaggcttg |
| 481 | agtaattatt ccatcataga caaacttgtg aatatagtgg atgaccttgt ggagtgcgtg |
| 541 | aaagaaaact catctaagga tctaaaaaaa tcattcaaga cccagaacc caggctcttt |
| 601 | actcctgaag aattctttag aatttttaat agatccattg atgccttcaa ggactttgta |
| 661 | gtggcatctg aaactagtga ttgtgtggtt tcttcaacat taagtcctga gaaagggaag |
| 721 | gccaaaaatc cccctggaga ctccagccta cactgggcag ccatggcatt gccagcattg |
| 781 | ttttctctta taattggctt tgcttttgga gccttatact ggaagaagag acagccaagt |
| 841 | cttacaaggg cagttgaaaa tatacaaatt aatgaagagg ataatgagat aagtatgttg |
| 901 | caagagaaag agagagagtt tcaagaagtg taattgtggc ttgtatcaac actgttactt |
| 961 | tcgtacattg gctggtaaca gttcatgttt gcttcataaa tgaagcagct ttaaacaaat |
| 1021 | tcatattctg tctggagtga cagaccacat ctttatctgt tcttgctacc catgacttta |
| 1081 | tatggatgat tcagaaattg gaacagaatg ttttactgtg aaactggcac tgaattaatc |
| 1141 | atctataaag aagaacttgc atggagcagg actctatttt aaggactgcg ggacttgggt |
| 1201 | ctcatttaga acttgcagct gatgttggaa gagaaagcac gtgtctcaga ctgcatgtac |
| 1261 | catttgcatg gctccagaaa tgtctaaatg ctgaaaaaac acctagcttt attcttcaga |
| 1321 | tacaaactgc agcctgtagt tatcctggtc tctgcaagta gatttcagct tggatagtga |
| 1381 | gggtaacaat ttttctcaaa gggatctgga aaaaatgttt aaaactcagt agtgtcagcc |
| 1441 | actgtacagt gtagaaagca gtgggaactg tgattggatt tggcaacatg tcagctttat |
| 1501 | agttgccgat tagtgatatg ggtctgattt cgatctcttc ctgatgtaaa ccatgctcac |
| 1561 | ccatatccca ctatacaaat gcaaatggtt gcctggttcc atttatgcaa gggagccagt |
| 1621 | actgaattat gccttggcag aggggagact ccaaaagagt catcgcagga agaagttaag |
| 1681 | aacactgaac atcagaacag tctgccaaga aggacattgg catcctggga aagtccgcct |
| 1741 | tttcccttga ccactatagg gtgtataaat cgtgtttgca aaatgtgtta tgatgtgttt |
| 1801 | atattctaaa actattacag agctatgtaa agggacttag gagaaaatgc tgaatgtaag |
| 1861 | atggtcccat ttcaatttcc accatgggag agcctaaaaa taaattatga catttagtat |
| 1921 | ctaaggttag aaaaccacgc ccacatgcta atatgggtgt tgaaaactag gttacttata |
| 1981 | atgcaaggaa tcaggaaact ttagttattt atagtataat caccattatc tgtttaaagg |
| 2041 | atccatttag ttaaaatcgg gcactctata ttcattaagg tttatgaatt aaaaagaaag |
| 2101 | ctttatgtag ttatgcatgt cagtttgcta tttaaaatgt gtgacagtgt ttgtcatatt |
| 2161 | aagagtgaat ttggcaggaa ttcccaagat ggacattgtg cttttaaact agaacttgta |
| 2221 | agacattatg tgaatatccc ttgccaattt tttttataat aagaaaacat ctgactaaag |
| 2281 | tcaaagaatg atttcttatg gtttattttg atgaaagttc ttttaacatg tcttgaatgt |
| 2341 | acacataaag gaatccaaag ctttccattc taacttaatc tttgtgataa cattattgcc |
| 2401 | atgttctaca accgtaagat gacagttttc aatgtagtga cacaaaaggg catgaaaaac |
| 2461 | taactgctag cttttccttc atttcaaaag tccaagaatt tctagtatat ttggatttta |

-continued

| SEQUENCES |
|---|

```
2521  gcttctgttc aaagcaaatc cagatgcaac tccagtaagt ggcctttgct cttttttgta
2581  ccaaagagcc cagatgattc ctacagtccc tttcttctct aacatgctgt ggttccttaa
2641  atatgagtaa tttctctaag atataaccca ggtgctttga gaagctgcat taaggtgttc
2701  aggccctcag atatcacatg gtacacttga ttagtaataa accagagat caatttaaat
2761  tgctgatagg tcctgtctca gtgtgtggca ttgactgttt tcaggaaaat agatacagat
2821  taatatgagt tatgcgtgta ggttgtgtat agattgagaa gatagatact tctcaatcta
2881  gtagtttgat ttatttaacc aatggtttca gtttgcttga gcatatgaaa atcctgctta
2941  atgtgcttaa gagtataata aatgtgtact tttgtcctca aacctagtag ctgggtttta
3001  acactcatgg acatggtctt aatcaatgga gttaaataaa caaattcagc aagttattaa
3061  atctgacatg gtaggagagg ggagatgtgt cctgcttatt aaatgtgttg gtccattgaa
3121  agttacatgg attgccaatt tttaaaacac taaagttgaa taaaatgcat gaacaataga
3181  aaaatgctga acattatttt ggatgctagc tgcttggaca ttaactgtgt tatttctgct
3241  ttgagatgaa aatatatatt tatctttgct tattttatcc cagatgtgtt ctgaatatcc
3301  ttcttcataa atcatggaaa actcactgct gagatagtaa accatgaaat cgccttttca
3361  gttggtgcca tgtatctgac agttccatct tggaaggttt caaaattacc ttttaaaatg
3421  atctcagaag tctgtagatt ctcaatgata ctgaaagctt tgcacctctt tggtagaaac
3481  caggtctatt tagaaaatgg ctttatgata aatgttgcct cctgagtgat aatgaagtgt
3541  tcctggatat tgtattgtaa tttaatgtgc ttaccacact gccacatttt aatgagtcag
3601  agaaaaatta attttcttc aatacaataa tagaacaagt agcctattct cttaaaaagt
3661  atgtgaaaag aaaattatga aaaaatatgc atacctaatg aagtattggt tttagtaaga
3721  attaaataca tttcattgag ctttaaagta cttttggagaa actttgggc acgttttcct
3781  actctaattc aactaaagtt ataaataaag agaaaaactc attcagaaat catggatttt
3841  aaaaatattt tactgcagcc aagttttcat ttcaaaatgt aatttcagtt tggagctttt
3901  aggcattatg tatatttaaa aaatatattc ttcaaaaatg cattttggca tggtgggatg
3961  gatgttgcaa agatatccg gagcctccag tctgtcatta actgatatgg taaatcacct
4021  ctcttctttg ggtctcaatt tttatttat ctatatggta aactcagaga tcactcctta
4081  ggggtgagtc ctattgcaat atgaccgaca aagaagacaa atagcattg aaactaaccc
4141  atacaaaata tccaactctg gattctgtga ataagtatct tgaccataaa aagtcattgc
4201  tgttcttgtt tctaatgtaa atagtgtcca ttagtaaaag tgaaattcag tcttaagtag
4261  ggtgaattgg atcaccattt acacaagaga tggctttttc ctttgcttga ataaacattt
4321  tggatcacct ccaaagaatg aaaaccagta gtacgtttta gtcatattag tcaggatgag
4381  aaactataag atgtgtgtaa catttggaaa tgcaccaaag tgagcgttta aatcttctca
4441  ttttattgaa aactaagagc agaaaatgta aaatgctcat gaaggttttg aatgccaaaa
4501  gatatttag aatcaattta taaagggta attcattaat tacactttaa aattggaaag
4561  tgggataaga aatctaaagt aaaccagctt atctttgaaa caatattatt ttgaaattgg
4621  ctttaaaata aaaccattca gattgaaatt ctaattagct catttgtgga gtttgatcac
4681  acaattcata atgttgctgc tttccattaa ctagtcttga aatgcctttg tttgtaaaaa
4741  taaaataatg gtactttcat tttataacaa ggtgttttt tcaagaaata atccatgcta
```

| SEQUENCES |
|---|
| 4801 aaatggatat ttgtgatcct gaaatgttta ctaagcattg taaatttatt tataactgcc |
| 4861 atctccaact acatccttat gatgttttta acaataaaat taaaacaact gttaaactaa |
| 4921 aaaccacacc gttttccagt acttgatctc tgagctacaa tactcactaa atataatttt |
| 4981 ccaatcaaaa tattctattc tatattctaa gggttaatat gtgattatag tgtccacttg |
| 5041 ccaccatttt tttaaatcaa tggacttgaa aagtattaat ttagatggat gcgcagatat |
| 5101 accctcagtt cagtcataga ttggagtttg catataataa tgtaaatgta tgtcgacact |
| 5161 attctaaata gttctattat gactgaaatt taattaaata aaaaaggttg taaaatgtga |
| 5221 tgtgtatgtg tatatactgt atgtgtactt tttaaaatag gtgtatgtcc caacccttt |
| 5281 ttatacaggt ttgaatttaa aattacatga tatatacata tactttattg ttctaaataa |
| 5341 agaattttat gcactctcaa aaaaaaaaaa aaaaaa |

Human tmSCF coding sequence (from NM_003994) (SEQ ID NO: 3)
ATGAAGAAGACACAAACTTGGATTCTCACTTGCATTTATCTTCAGCTGCT
CCTATTTAATCCTCTCGTCAAAACTGAAGGGATCTGCAGGAATCGTGTGA
CTAATAATGTAAAAGACGTCACTAAATTGGTGGCAAATCTTCCAAAAGAC
TACATGATAACCCTCAAATATGTCCCCGGGATGGATGTTTTGCCAAGTCA
TTGTTGGATAAGCGAGATGGTAGTACAATTGTCAGACAGCTTGACTGATC
TTCTGGACAAGTTTTCAAATATTTCTGAAGGCTTGAGTAATTATTCCATC
ATAGACAAACTTGTGAATATAGTGGATGACCTTGTGGAGTGCGTGAAAGA
AAACTCATCTAAGGATCTAAAAAAATCATTCAAGAGCCCAGAACCCAGGC
TCTTTACTCCTGAAGAATTCTTTAGAATTTTTAATAGATCCATTGATGCC
TTCAAGGACTTTGTAGTGGCATCTGAAACTAGTGATTGTGTGGTTTCTTC
AACATTAAGTCCTGAGAAAGGGAAGGCCAAAAATCCCCCTGGAGACTCCA
GCCTACACTGGGCAGCCATGGCATTGCCAGCATTGTTTTCTCTTATAATT
GGCTTTGCTTTTGGAGCCTTATACTGGAAGAAGAGACAGCCAAGTCTTAC
AAGGGCAGTTGAAAATATACAAATTAATGAAGAGGATAATGAGATAAGTA
TGTTGCAAGAGAAAGAGAGAGAGTTTCAAGAAGTGTAA Membrane scaffold protein 1D1 (SEQ ID NO: 4)
GHHHHHHHDYDIPTTENLYFQGSTFSKLREQLGPVTQEFWDNLEKETEGLRQEMSKDLEEVKAKVQPYLDDFQKK
WQEEMELYRQKVEPLRAELQEGARQKLHELQEKLSPLGEEMRDRARAHVDALRTHLAPYSDELRQRLAARLEALK
ENGGARLAEYHAKATEHLSTLSEKAKPALEDLRQGLLPVLESFKVSFLSALEEYTKKLNTQ Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A lipid nanodisc composition comprising: a membrane scaffold protein; a lipid; and a transmembrane stem cell factor (tmSCF) polypeptide; wherein the composition is encapsulated in a biodegradable microcapsule or microbead wherein the composition is effective in treating peripheral vascular disease (PVP) or promoting angiogenesis.

2. The composition of claim 1, wherein the lipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, phosphatidyl choline (PC); phosphatidyl ethanolamine (PE), phosphatidyl inositol (PI); dihexanoyl phosphatidyl choline (DHPC), dipalmitoyl phosphatidyl ethanolamine, dipalmitoyl phosphatidyl inositol; dimyristoyl phosphatidyl ethanolamine; dimyristoyl phosphatidyl inositol; dihexanoyl phosphatidyl ethanolamine; dihexanoyl phosphatidyl inositol; 1-palmitoyl-2-oleoyl-phosphatidyl ethanolamine; 1-palmitoyl-2-oleoyl-phosphatidyl inositol, and mixtures thereof.

3. The composition of claim 1, wherein the lipid comprises 1-palmitoyl-2-oleoyl-sn-glycero-3-phosphocholine (POPC).

4. The composition of claim 1, wherein the membrane scaffold protein to lipid weight ratio is about 1:65.

5. The composition of claim 1, wherein the membrane scaffold protein comprises a 1D1 protein.

6. The composition of claim 1, wherein the nanodisc is from about 10 nm to about 400 nm in size.

7. The composition of claim 1, wherein the transmembrane stem cell factor (tmSCF) polypeptide is human tmSCF, or a variant thereof.

8. The composition of claim 1, wherein the transmembrane stem cell factor (tmSCF) polypeptide comprises SEQ ID NO:1, or an amino acid sequence that is at least 65% identical to SEQ ID NO:1.

9. The composition of claim 1, wherein the microcapsule or microbead comprises a biocompatible hydrogel.

10. The composition of claim 9, wherein the biocompatible hydrogel comprises a polysaccharide.

11. The composition of claim 9, wherein the biocompatible hydrogel comprises alginate.

12. The composition of claim 1 wherein the microcapsule or microbead is from 1 μm in diameter up to 3 mm in diameter.

* * * * *

SEQUENCE LISTING

<160> NUMBER OF SEQ ID NOS: 4

<210> SEQ ID NO 1
<211> LENGTH: 245
<212> TYPE: PRT
<213> ORGANISM: Homo sapiens

<400> SEQUENCE: 1

Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu

```
            50                  55                  60
Pro Ser His Cys Trp Ile Ser Glu Met Val Val Gln Leu Ser Asp Ser
 65                  70                  75                  80

Leu Thr Asp Leu Leu Asp Lys Phe Ser Asn Ile Ser Glu Gly Leu Ser
                 85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
        115                 120                 125

Ser Pro Glu Pro Arg Leu Phe Thr Pro Glu Glu Phe Phe Arg Ile Phe
    130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Gly Lys Ala
                165                 170                 175

Lys Asn Pro Pro Gly Asp Ser Ser Leu His Trp Ala Ala Met Ala Leu
            180                 185                 190

Pro Ala Leu Phe Ser Leu Ile Ile Gly Phe Ala Phe Gly Ala Leu Tyr
        195                 200                 205

Trp Lys Lys Arg Gln Pro Ser Leu Thr Arg Ala Val Glu Asn Ile Gln
    210                 215                 220

Ile Asn Glu Glu Asp Asn Glu Ile Ser Met Leu Gln Glu Lys Glu Arg
225                 230                 235                 240

Glu Phe Gln Glu Val
            245

<210> SEQ ID NO 2
<211> LENGTH: 5376
<212> TYPE: DNA
<213> ORGANISM: Homo sapiens

<400> SEQUENCE: 2
gggcttcgct cgccgcctcg cgccgagact agaagcgctg cgggaagcag ggacagtgga      60
gagggcgctg cgctcgggct acccaatgcg tggactatct gccgccgctg ttcgtgcaat     120
atgctggagc tccagaacag ctaaacggag tcgccacacc actgtttgtg ctggatcgca     180
gcgctgcctt tccttatgaa gaagacacaa acttggattc tcacttgcat ttatcttcag     240
ctgctcctat ttaatcctct cgtcaaaact gaagggatct gcaggaatcg tgtgactaat     300
aatgtaaaag acgtcactaa attggtggca aatcttccaa aagactacat gataaccctc     360
aaatatgtcc ccgggatgga tgttttgcca agtcattgtt ggataagcga gatggtagta     420
caattgtcag acagcttgac tgatcttctg acaagttttt caaatatttc tgaaggcttg     480
agtaattatt ccatcataga caaacttgtg aatatagtgg atgaccttgt ggagtgcgtg     540
aaagaaaact catctaagga tctaaaaaaa tcattcaaga gcccagaacc caggctcttt     600
actcctgaag aattctttag aattttaat agatccattg atgccttcaa ggactttgta     660
gtggcatctg aaactagtga ttgtgtggtt cttcaacat aagtcctga aaagggaag       720 gccaaaaatc cccctggaga ctccagccta cactgggcag ccatggcatt gccagcattg     780
ttttctctta taattggctt tgcttttgga gccttatact ggaagaagag acagccaagt     840
cttacaaggg cagttgaaaa atacaaaatt aatgaagagg ataatgagat aagtatgttg     900
caagagaaag agagagagtt tcaagaagtg taattgtggc ttgtatcaac actgttactt     960
tcgtacattg gctggtaaca gttcatgttt gcttcataaa tgaagcagct ttaaacaaat    1020
```

```
tcatattctg tctggagtga cagaccacat ctttatctgt tcttgctacc catgacttta    1080
tatggatgat tcagaaattg aacagaatg ttttactgtg aaactggcac tgaattaatc     1140
atctataaag aagaacttgc atggagcagg actctatttt aaggactgcg ggacttgggt    1200
ctcatttaga acttgcagct gatgttggaa gagaaagcac gtgtctcaga ctgcatgtac    1260
catttgcatg gctccagaaa tgtctaaatg ctgaaaaaac acctagcttt attcttcaga    1320
tacaaactgc agcctgtagt tatcctggtc tctgcaagta gatttcagct tggatagtga    1380
gggtaacaat ttttctcaaa gggatctgga aaaatgtttt aaaactcagt agtgtcagcc    1440
actgtacagt gtagaaagca gtgggaactg tgattggatt tggcaacatg tcagctttat    1500
agttgccgat tagtgatatg ggtctgattt cgatctcttc ctgatgtaaa ccatgctcac    1560
ccatatccca ctatacaaat gcaaatggtt gcctggttcc atttatgcaa gggagccagt    1620
actgaattat gccttggcag aggggagact ccaaagagt catcgcagga agaagttaag     1680
aacactgaac atcagaacag tctgccaaga aggacattgg catcctggga aagtccgcct    1740
tttcccttga ccactatagg gtgtataaat cgtgtttgca aaatgtgtta tgatgtgttt    1800
atattctaaa actattacag agctatgtaa agggacttag gagaaaatgc tgaatgtaag    1860
atggtcccat ttcaatttcc accatgggag agcctaaaaa taaattatga catttagtat    1920
ctaaggttag aaaaccacgc ccacatgcta atatgggtgt tgaaaactag gttacttata    1980
atgcaaggaa tcaggaaact ttagttattt atagtataat caccattatc tgtttaaagg    2040
atccatttga ttaaaatcgg gcactctata ttcattaagg tttatgaatt aaaaagaaag    2100
ctttatgtag ttatgcatgt cagtttgcta tttaaaatgt gtgacagtgt ttgtcatatt    2160
aagagtgaat ttggcaggaa ttcccaagat ggacattgtg cttttaaact agaacttgta    2220
agacattatg tgaatatccc ttgccaattt tttttataat aagaaaacat ctgactaaag    2280
tcaaagaatg atttcttatg gtttattttg atgaaagttc ttttaacatg tcttgaatgt    2340
acacataaag gaatccaaag ctttccattc taacttaatc tttgtgataa cattattgcc    2400
atgttctaca accgtaagat gacagttttc aatgtagtga cacaaagggg catgaaaaac    2460
taactgctag ctttcctttc atttcaaaag tccaagaatt tctagtatat ttggatttta    2520
gcttctgttc aaagcaaatc cagatgcaac tccagtaagt ggcctttgct cttttttgta    2580
ccaaagagcc cagatgattc ctacagtccc tttcttctct aacatgctgt ggttccttaa    2640
atatgagtaa tttctctaag atataaccca ggtgctttga gaagctgcat taaggtgttc    2700
aggccctcag atatcacatg gtacacttga ttagtaataa aaccagagat caatttaaat    2760
tgctgatagg tcctgtctca gtgtgtggca ttgactgttt tcaggaaaat agatacagat    2820
taatatgagt tatgcgtgta ggttgtgtat agattgagaa gatagatact tctcaatcta    2880
gtagtttgat ttatttaacc aatggtttca gtttgcttga gcatatgaaa atcctgctta    2940
atgtgcttaa gagtataata aatgtgtact tttgtcctca aacctagtag ctgggtttta    3000
acactcatgg acatggtctt aatcaatgga gttaaataaa caaattcagc aagttattaa    3060
atctgacatg gtaggagagg ggagatgtgt cctgcttatt aaatgtgttg gtccattgaa    3120
agttacatgg attgccaatt tttaaaacac taaagttgaa taaaatgcat gaacaataga    3180
aaaatgctga acattatttt ggatgctagc tgcttggaca ttaactgtgt tatttctgct    3240
ttgagatgaa aatatatatt tatctttgct tatttatcc cagatgtgtt ctgaatatcc     3300
ttcttcataa atcatggaaa actcactgct gagatagtaa accatgaaat cgccttttca    3360
```

-continued

```
gttggtgcca tgtatctgac agttccatct tggaaggttt caaaattacc ttttaaaatg   3420
atctcagaag tctgtagatt ctcaatgata ctgaaagctt tgcacctctt tggtagaaac   3480
caggtctatt tagaaaatgg ctttatgata aatgttgcct cctgagtgat aatgaagtgt   3540
tcctggatat tgtattgtaa tttaatgtgc ttaccacact gccacatttt aatgagtcag   3600
agaaaaatta attttcttc aatacaataa tagaacaagt agcctattct cttaaaaagt   3660
atgtgaaaag aaaattatga aaaaatatgc atacctaatg aagtattggt tttagtaaga   3720
attaaataca tttcattgag ctttaaagta ctttggagaa actttggggc acgttttcct   3780
actctaattc aactaaagtt ataaataaag agaaaaactc attcagaaat catggatttt   3840
aaaaatattt tactgcagcc aagttttcat ttcaaaatgt aatttcagtt tggagctttt   3900
aggcattatg tatatttaaa aaatatattc ttcaaaaatg cattttggca tggtgggatg   3960
gatgttgcaa aagatatccg gagcctccag tctgtcatta actgatatgg taaatcacct   4020
ctcttctttg ggtctcaatt ttttatttat ctatatggta aactcagaga tcactcctta   4080
ggggtgagtc ctattgcaat atgaccgaca agaagacaa aatagcattg aaactaaccc   4140
atacaaaata tccaactctg gattctgtga ataagtatct tgaccataaa aagtcattgc   4200
tgttcttgtt tctaatgtaa atagtgtcca ttagtaaaag tgaaattcag tcttaagtag   4260
ggtgaattgg atcaccattt acacaagaga tggcttttc ctttgcttga ataaacattt   4320
tggatcacct ccaaagaatg aaaaccagta gtacgtttta gtcatattag tcaggatgag   4380
aaactataag atgtgtgtaa catttggaaa tgcaccaaag tgagcgttta atcttctca   4440 ttttattgaa aactaagagc agaaaatgta aaatgctcat gaaggttttg aatgccaaaa   4500
gatattttag aatcaattta taagggggta attcattaat tacactttaa aattggaaag   4560
tgggataaga aatctaaagt aaaccagctt atctttgaaa caatattatt ttgaaattgg   4620
ctttaaaata aaaccattca gattgaaatt ctaattagct catttgtgga gtttgatcac   4680
acaattcata atgttgctgc tttccattaa ctagtcttga aatgcctttg tttgtaaaaa   4740
taaaataatg gtactttcat tttataacaa ggtgtttttt tcaagaaata atccatgcta   4800
aaatggatat ttgtgatcct gaaatgttta ctaagcattg taaatttatt tataactgcc   4860
atctccaact acatccttat gatgtttta acaataaaat taaaacaact gttaaactaa   4920
aaaccacacc gttttccagt acttgatctc tgagctacaa tactcactaa atataatttt   4980
ccaatcaaaa tattctattc tatattctaa gggttaatat gtgattatag tgtccacttg   5040
ccaccatttt tttaaaatcaa tggacttgaa aagtattaat ttagatggat gcgcagatat   5100
accctcagtt cagtcataga ttggagtttg catataataa tgtaaatgta tgtcgacact   5160
attctaaata gttctattat gactgaaatt taattaaata aaaaggttg taaaatgtga   5220 tgtgtatgtg tatatactgt atgtgtactt tttaaaatag gtgtatgtcc caacccttt   5280 ttatacaggt ttgaatttaa aattacatga tatatacata tacttttatgt ttctaaataa   5340 agaatttttat gcactctcaa aaaaaaaaaa aaaaaa                            5376
```

<210> SEQ ID NO 3
<211> LENGTH: 738
<212> TYPE: DNA
<213> ORGANISM: Homo sapiens

<400> SEQUENCE: 3

```
atgaagaaga cacaaacttg gattctcact tgcatttatc ttcagctgct cctatttaat     60
cctctcgtca aaactgaagg gatctgcagg aatcgtgtga ctaataatgt aaaagacgtc    120
```

```
actaaattgg tggcaaatct tccaaaagac tacatgataa ccctcaaata tgtccccggg    180
atggatgttt tgccaagtca ttgttggata agcgagatgg tagtacaatt gtcagacagc    240
ttgactgatc ttctggacaa gttttcaaat atttctgaag gcttgagtaa ttattccatc    300
atagacaaac ttgtgaatat agtggatgac cttgtggagt gcgtgaaaga aaactcatct    360
aaggatctaa aaaatcatt caagagccca gaacccaggc tctttactcc tgaagaattc    420
tttagaattt ttaatagatc cattgatgcc ttcaaggact ttgtagtggc atctgaaact    480
agtgattgtg tggtttcttc aacattaagt cctgagaaag ggaaggccaa aaatccccct    540
ggagactcca gcctacactg ggcagccatg gcattgccag cattgttttc tcttataatt    600
ggctttgctt ttggagcctt atactggaag aagagacagc caagtcttac aagggcagtt    660
gaaaatatac aaattaatga agaggataat gagataagta tgttgcaaga aaagagaga    720 gagtttcaag aagtgtaa                                                 738
```

<210> SEQ ID NO 4
<211> LENGTH: 211
<212> TYPE: PRT
<213> ORGANISM: Artificial Sequence
<220> FEATURE:
<223> OTHER INFORMATION: Synthetic construct
<400> SEQUENCE: 4

```
Gly His His His His His His Asp Tyr Asp Ile Pro Thr Thr Glu
1               5                   10                  15

Asn Leu Tyr Phe Gln Gly Ser Thr Phe Ser Lys Leu Arg Glu Gln Leu
            20                  25                  30

Gly Pro Val Thr Gln Glu Phe Trp Asp Asn Leu Glu Lys Glu Thr Glu
        35                  40                  45

Gly Leu Arg Gln Glu Met Ser Lys Asp Leu Glu Glu Val Lys Ala Lys
    50                  55                  60

Val Gln Pro Tyr Leu Asp Asp Phe Gln Lys Lys Trp Gln Glu Glu Met
65                  70                  75                  80

Glu Leu Tyr Arg Gln Lys Val Glu Pro Leu Arg Ala Glu Leu Gln Glu
                85                  90                  95

Gly Ala Arg Gln Lys Leu His Glu Leu Gln Glu Lys Leu Ser Pro Leu
            100                 105                 110

Gly Glu Glu Met Arg Asp Arg Ala Arg Ala His Val Asp Ala Leu Arg
        115                 120                 125

Thr His Leu Ala Pro Tyr Ser Asp Glu Leu Arg Gln Arg Leu Ala Ala
    130                 135                 140

Arg Leu Glu Ala Leu Lys Glu Asn Gly Gly Ala Arg Leu Ala Glu Tyr
145                 150                 155                 160

His Ala Lys Ala Thr Glu His Leu Ser Thr Leu Ser Glu Lys Ala Lys
                165                 170                 175

Pro Ala Leu Glu Asp Leu Arg Gln Gly Leu Leu Pro Val Leu Glu Ser
            180                 185                 190

Phe Lys Val Ser Phe Leu Ser Ala Leu Glu Glu Tyr Thr Lys Lys Leu
        195                 200                 205

Asn Thr Gln
    210
```